US009730894B2

(12) United States Patent
Miller et al.

(10) Patent No.: US 9,730,894 B2
(45) Date of Patent: Aug. 15, 2017

(54) STABILIZED HME COMPOSITION WITH SMALL DRUG PARTICLES

(71) Applicant: BOARD OF REGENTS, THE UNIVERSITY OF TEXAS SYSTEM, Austin, TX (US)

(72) Inventors: Dave A. Miller, Austin, TX (US); Jason T. McConville, Austin, TX (US); James W. McGinity, Austin, TX (US); Robert O. Williams, III, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/341,217

(22) Filed: Nov. 2, 2016

(65) Prior Publication Data

US 2017/0119669 A1 May 4, 2017

Related U.S. Application Data

(62) Division of application No. 11/718,620, filed as application No. PCT/US2005/040535 on Nov. 9, 2005, now Pat. No. 9,504,658.

(60) Provisional application No. 60/681,279, filed on May 16, 2005, provisional application No. 60/626,400, filed on Nov. 9, 2004.

(51) Int. Cl.
*A61K 9/14* (2006.01)
*A61P 43/00* (2006.01)
*A61K 31/496* (2006.01)
*A61K 38/13* (2006.01)
*A61K 31/58* (2006.01)
*A61K 31/55* (2006.01)

(52) U.S. Cl.
CPC ............ *A61K 9/146* (2013.01); *A61K 31/496* (2013.01); *A61K 31/55* (2013.01); *A61K 31/58* (2013.01); *A61K 38/13* (2013.01)

(58) Field of Classification Search
None
See application file for complete search history.

(56) References Cited

U.S. PATENT DOCUMENTS

| 6,068,855 | A | 5/2000 | Leslie et al. |
| 6,346,533 | B1 | 2/2002 | Cha |
| 6,391,338 | B1 | 5/2002 | Frisbee |
| 2001/0007678 | A1 | 7/2001 | Baert et al. |
| 2001/0048946 | A1 | 12/2001 | Chebre-Sellassie |
| 2001/0055622 | A1 | 12/2001 | Burrell et al. |
| 2003/0059465 | A1 | 3/2003 | Unger et al. |
| 2003/0104068 | A1 | 6/2003 | Mathiowitz et al. |

FOREIGN PATENT DOCUMENTS

| CA | 2240161 | 11/1997 |
| WO | WO 02/35991 | 5/2002 |
| WO | WO 2007/001451 | 1/2007 |

OTHER PUBLICATIONS

Aitken-Nichol, et al., "Hot Melt Extrusion of Acrylic Films," Pharmaceutical Research, 1996; 13(5): 804-808.
Bleich, et al., "Production of Drug Loaded Microparticles by the Use of Supercritical Gases with the Aerosol Solvent Extraction System (ASES) Process," Journal of Microencapsulation, 1996; 13(2):131-139.
CAS 84625-61-6 Itraconazole, accessed Sep. 25, 2015.
Chattopadhy AY, et al., "Production of Griseofulvin Nanoparticles Using Supercritical C02 Antisolvent with Enhanced Mass Transfer," International Journal of Pharmaceutics, 2001; 228(1-2):19-31.
Chen, et al., "Preparation of Cyclosporine A Nanoparticles by Evaporative Precipitation into Aqueous Solution," International Journal of Pharmaceutics, 2002; 242(1-2):3-14.
De Braband ER, et al., "Development and Evaluation of Sustained Release Mini-Matrices Prepared via Hot Melt Extrusion," Journal of Controlled Release, 2003; 89(2): 235-247.
De Brabander, C, et al., "Bioavailability of Ibuprofen from Hot-Melt Extruded Mini-Matrices," International Journal of Pharmaceutics, 2004; 271(1-2):77-84.
Evans, et al., "Preparation of Nanostructured Particles of Poorly Water Soluble Drugs via a Novel Ultra-Rapid Freezing Technology," Polymeric Materials Science and Engineering, 2003; 89:742.
Extended European Search Report issued in corresponding European Application No. 05858310.5, dated Sep. 8, 2016.

(Continued)

*Primary Examiner* — Robert A Wax
*Assistant Examiner* — Danah Al-Awadi
(74) *Attorney, Agent, or Firm* — Parker Highlander PLLC

(57) ABSTRACT

A hot-melt extruded composition having finely divided drug-containing particles dispersed within a polymeric and/or lipophyllic carrier matrix is provided. The carrier softens or melts during hot-melt extrusion but it does not dissolve the drug-containing particles during extrusion. As a result, a majority or at least 90% wt. of the drug-containing particles in the extrudate are deaggregated during extrusion into essentially primary crystalline and/or amorphous particles. PEO is a suitable carrier material for drugs insoluble in the solid state in this carrier. Various functional excipients can be included in the carrier system to stabilize the particle size and physical state of the drug substance in either a crystalline and/or amorphous state. The carrier system is comprised of at least one thermal binder, and may also contain various functional excipients, such as: super-disintegrants, antioxidants, surfactants, wetting agents, stabilizing agents, retardants, or similar functional excipients. A hydrophilic polymer, such as hydroxypropyl methylcellulose (HPMC E15), polyvinyl alcohol (PVA), or poloxamer, and/or a surfactant, such as sodium lauryl sulfate (SLS), can be included in the composition. A process for preparing the extrudate is conducted at a temperature approximating or above the softening or melting temperature of the matrix and below the point of solubilization of drug-containing particles in the carrier system, and below the recrystallization point in the case of amorphous fine drug particles.

28 Claims, 20 Drawing Sheets

(56) References Cited

OTHER PUBLICATIONS

Forster, et al., "Characterization of Glass Solutions of Poorly Water Soluble Drugs Produced by Melt Extrusion with Hydrophilic Amorphous Polymers," Journal of Pharmacy and Pharmacology, 2001; 53:303-315.
French. et al., "The influence of Formulation of Emission, Deaggregation and Deposition of Dry Powders for Inhalation," Journal of Aerosol Science, 1996; 27:769-783.
Ghaderi, et al,"Preparation of Biodegradable Microparticles Using Solution-Enhanced Dispersion by Supercritical Fluids (SEDS)," Phannaceutical Research, 1999; 16(6):676-681.
Hu, et al., "Improvement of Dissolution Rates of Poorly Water Soluble APIs Using Novel Spray Freezing into Liquid Technology," Pharmaceutical Research, 2002. 19(9):1278-1284.
Hu, et al., "Rapid Release Tablet Formulation of Micronized Danazol Powder Produced by Spray-Freezing into Liquid (SFL)," Journal of Drug Delivery Science and Technology, 2004; 14(4):305-311.
Hulsmann, et al, "Melt Extrusion—An Alternative Method for Enhancing the Dissolution Rate of 17(Beta)-Estradiol Hemihydrate," European Journal of Pharmaceutics and Biopharmaceutics, 2000; 49(3):237-242.
International Preliminary Report on Patentability for PCT/US2005/040535, dated Feb. 12, 2009, 7 pages.
International Search Report for PCT/US2005/040535, dated Apr. 1, 2008, 4 pages.
Kearney, et al., "Effect of Polyvinylpyrrolidone on the Crystallinity and Dissolution Rate of Solid Dispersions of the Antiinflammatory Cl-987," International Journal of Pharmaceutics, 1994; 104(2):169-174.
Liu, et al., "Deaggregation During the Dissolution of Benzodiazepines in Interactive Mixtures," Journal of Pharmaceutical Science, 1998; 87( 12): 1632-1638.
Liversidge, et al, "Particle Size Reduction for Improvement of Oral Bioavailability of Hydrophobic Drugs. Part 1: Absolute Oral Bioavailability of Nanocrystalline Danazol in Beagle Dogs," International Journal of Pharmaceutics, 1995; 125:91-97.
Liversidge, GG, et al., "Drug Particle Size Reduction for Decreasing Gastric Irritancy and Enhancing Absorption of Naproxen in Rats," International Journal of Pharmaceutics, 1995; 125(2):309-313.
Nykamp, et al., "Jet Milling—A New Technique for Microparticle Preparation," International Journal of Pharmaceutics, 2002; 242(1-2):79-86.
Palakodaty, et al., "Phase Behavioral Effects on Particle Formation Processes Using Supercritical Fluids," Pharmaceutical Research, 1999; 16(7):76-985.
Phillips, et al., "Rapid Expansion from Supercritical Solutions: Application to Pharmaceutical Processes," International Journal of Pharmaceutics, 1993; 94(1-3):1-10.
Rambali, et al., "Ilraconazole Formulation Studies of the Melt-Extrusion Process with Mixture Design," Drug Development and Industrial Pharmacy, 2003; 29(6):641-652.
Repka, et al., "Hot-Melt Extruded Films for Transmucosal & Transdermal Durg Delivery Applications," Drug Delivery Technology, 2004; 4(7):40, 42, 44-47.
Reverchon, Ernesto, "Supercritica Antisolvent Precipitation of Micro- and Nano-Particles," The Journal of Supercritical Fluids, 1999; 15(1 ):1-21.
Six, et al., "Characterization of Solid Dispersions of ltraconazole and Hydroxypropylmethylcellulose Prepared by Melt Extrusion, Part 11," Pharmaceutical Research, 2003; 20(7): 1047-1054.
Six, et al., "Identification of Phase Separation in Solid Dispersions of ltraconazole and Eudragit E100 Using Microthermal Analysis," Pharmaceutical Research, 2003; 20(1)135-138.
Six, et al., "Increased Physical Stability and Improved Dissolution Properties of ltraconazole, a Class II Drug, by Solid Dispersions that Combine Fast- and Slow-Dissolving Polymers," Journal of Pharmaceutical Sciences, 2004; 93 (1):124-131.
Six, et al., "Thermal Properties of Hot-Stage Extrudates of ltraconazole and Eudragit E100Phase Separation and Polymorphism," Journal of Thermal Analysis and Calorimetry, 2002; 68:591-601.
Ticehurst, et al., "Characterisation of the lnftuence of Micronisation on the Crystallinity and Physical Stability of Revatropate Hydrobromide," International Journal of Pharmaceutics, 2000; 193: 247-259.
Verreck, et al., "Characterization of Solid Dispersions of ltraconazole and Hydroxypropylmethylcellulose Prepared by Melt Extrusion—Part I," International Journal of Pharmaceutics, 2003; 251 (1-2):165-174.
Verreck, et al., "The Use of Three Different Solid Dispersion Formulations—Melt Extrusion, Film-Coaled Beads, and a Glass Thermoplastic System—To Improve the Bioavailability of a Novel Microsomal Triglyceride Transfer Protein Inhibitor," Journal of Pharmaceutical Sciences, 2004; 93(5):1217-1228.
Written Opinion of the International Searching Authority for or PCT/US2005/040535, dated Apr. 1, 2008, 5 pages.
Young et al., "Production of spherical pellets by a hot-melt extrusion and spheronization process", International Journal of Pharmaceutics, 242: 87-92, 2002.
Zhang, et al., "Properties of Sustained-Release Tablets Prepared by Hot-Melt Extrusion," Pharmaceutical Development and Technology, 1999; 4(2):241-250.
Zhang. et al., "Properties of Hot-Melt Extruded Theophylline Tablets Containing Poly(Vinyl Acetate)," Drug Development and Industrial Pharmacy, 2000; 26(9):931 -942.
Zimon, AD, "Adhesion of Dust and Powder", New York: Consultants Bureau (Plenum), 1982; pp. 93-144.

STABILIZED HME COMPOSITION WITH SMALL DRUG PARTICLES

This application is a divisional of U.S. application Ser. No. 11/718,620, filed Nov. 19, 2007, now U.S. Pat. No. 9,504,658, which is a national phase application under 35 U.S.C. §371 of International Application No. PCT/US2005/040535, filed Nov. 9, 2005, which claims priority to U.S. provisional application No. 60/681,279, filed May 16, 2005, and U.S. provisional application No. 60/626,400, filed Nov. 9, 2005. The entire text of each of the above referenced disclosures is specifically incorporated herein by reference.

FIELD OF THE INVENTION

The present invention concerns a hot-melt extruded pharmaceutical composition comprising a therapeutic compound dispersed as fine particles in a stabilizing and non-solubilizing carrier system and a method of preparation thereof. The invention also concerns a process of preparing a hot-melt extruded pharmaceutical composition wherein small amorphous or crystalline particles of a therapeutic compound are dispersed as individual particles during hot-melt extrusion and after storage for extended periods of time. The hot-melt extruded composition provides stable release properties of the therapeutic compound over an extended period of storage.

BACKGROUND OF THE INVENTION

Many researchers have utilized hot-melt extrusion techniques to produce pharmaceutical preparations in various forms. Zhang and McGinity utilized hot-melt extrusion to produce sustained release matrix tablets with PEO and polyvinyl acetate, and more generally non-film preparations with polyethylene oxide (PEO) (1-3). Kothrade et al. demonstrated a method of producing solid dosage forms of active ingredients in a vinyllactam co-polymeric binder by hot-melt extrusion (4). Aitken-Nichol et al. used hot-melt extrusion methods to produce acrylic polymer films containing the active lidocaine HCl (5). Grabowski et al. produced solid pharmaceutical preparations of actives in low-substituted hydroxypropyl cellulose using hot-melt extrusion techniques (6). Repka and McGinity used hot-melt extrusion processes to produce bioadhesive films for topical and mucosal adhesion applications for controlled drug delivery to various mucosal sites (7, 8). Robinson et al. produced effervescent granules with controlled rate of effervescence using hot melt extrusion techniques (3). Breitenbach and Zettler produced solid spherical materials containing biologically active substances via hot-melt extrusion (9). De Brabander et al. demonstrated sustained release mini-matrices by utilizing hot-melt extrusion techniques (10, 11).

Pharmaceutical formulations comprised of active compounds finely and homogenously dispersed in one or more polymeric carriers have been described as solid dispersions, glass solutions, molecular dispersions, and solid solutions. The term solid dispersion has been used as a general term to describe pharmaceutical preparations in which the active compound is dispersed in an inert excipient carrier in a size range from course to fine. Glass solution, molecular dispersion, and solid solution refer specifically to preparations in which amorphous forms of a crystalline active compound are formed in-situ and dispersed within the polymer matrix during the hot-melt extrusion process.

Many researchers have produced such preparations with various active compounds and polymeric carriers using hot-melt extrusion techniques. Rosenberg and Breitenbach have produced solid solutions by melt extruding the active substance in a nonionic form together with a salt and a polymer, such as polyvinylpyrrolidone (PVP), vinylpyrrolidinone/vinylacetate (PVPVA) copolymer, or a hydroxyalkylcellulose (12). Six et al., Brewster et al., Baert et al., and Verreck et al. have produced solid dispersions of itraconazole with improved dissolution rates by hot-melt extrusion with various polymeric carriers including hydroxypropylmethylcellulose, Eudragit E100, PVPVA, and a combination of Eudragit E100 and PVPVA (13-19). Rambaldi et al. produced solid dispersions of itraconazole by hot-melt extrusion with hydroxypropyl-beta-cyclodextrin and hydroxypropylmethylcellulose for the improvement of aqueous solubility (20). Verreck et al. produced solid dispersions of a water-insoluble microsomal triglyceride transfer protein inhibitor with improved bioavailability by hot-melt extrusion (21). Hulsmann et al. produced solid dispersions of the poorly water soluble drug 17 β-estradiol with increased dissolution rate by hot melt extrusion with polymeric carriers such as polyethylene glycol, PVP, and PVPVA along with various non-polymeric additives (22). Forster et al. produced amorphous glass solutions with the poorly water soluble drugs indomethacin, lacidipine, nifedipine, and tolbutamide in PVP and PVPVA demonstrating improved dissolution compared with the crystalline forms (23). In this article, it is also seen that after storage of the extrudates at 25° C. and 75% relative humidity only compositions containing indomethacin and polymer in a one to one ratio remained completely amorphous. Formulations of the remaining drugs and formulations with increased indomethacin concentration showed recrystallization on storage. This recrystallization was shown to significantly decrease the dissolution rate of the active. It should also be noted that stability studies were not performed at elevated temperatures in this study. It would be expected that elevated temperatures would increase the occurrence and extent of recrystallization.

The previous reference reveals the inherent instability of amorphous dispersions produced by hot-melt extrusion techniques. Although many articles demonstrate the production of amorphous solid dispersions and the resulting improvement of drug dissolution rate, very few discuss the stability of such preparations on storage. From the work of Foster et al. and an understanding of the thermodynamics of amorphous systems, it can be concluded that recrystallization of amorphous solid dispersion formulations on storage is a common problem. The amorphous state is thermodynamically metastable, and therefore it is expected that amorphous compounds will assume a stable crystalline conformation with time, as well as in response to perturbations such as elevations in temperature and exposure to moisture. In an extruded formulation, amorphous drug particles will agglomerate and crystallize with increasing storage time, elevated temperature, or exposure to moisture, essentially precipitating out of the carrier. This progression towards phase separation during storage results in a time dependant dissolution profile. A change in dissolution rate with time precludes the successful commercialization of a pharmaceutical product.

The article by Foster et al. also demonstrates the limitation of drug loading in amorphous solid dispersions by hot-melt extrusion. It is seen in this article that recrystallization of indomethacin on storage is induced when the concentration of indomethacin is increased from 1:1 to 4:1 drug to polymer ratio. Six et al. demonstrated immiscibility of itraconazole and Eudragit E100 when extruded at 140° C.

and phase separation on processing at concentrations greater than 13% and 20% (w/w) when extruded at 168° C. and 180° C., respectively (14-16). Six et al. also demonstrated a single phase system of itraconazole and PVPVA at drug concentrations up to 80% (w/w), however only a slight improvement of the dissolution rate was achieved (16). Kearney et al. showed phase separation of an anti-inflammatory drug, CI-987, in PVP at drug concentrations greater than 19% (w/w) for solid dispersions prepared by solvent evaporation methods (24). Verreck et al. demonstrated an amorphous dispersion of itraconazole in HPMC at a concentration of 40% drug, with improved dissolution rate and chemical and physical stability for up to 6 months at various temperature and humidity conditions (17). In a follow up article, Six et al. showed phase separation of itraconazole from identical HPMC carrier systems at a concentration of 60% drug (13).

The difficulty of producing stable single phase amorphous dispersions of high drug loading can be seen from references such as those given above. The appearance of a second phase of the active compound on processing or on storage would result in a time dependent biphasic dissolution profile, and would therefore not be considered an acceptable pharmaceutical preparation.

Although there have been many reports of successful production of solid dispersions by hot-melt extrusion that show improved dissolution rates of poorly water soluble drugs, the absence of numerous marketed products based on this technology is evidence that stability problems remain a major obstacle for successful commercialization of such a pharmaceutical preparation.

There are several methods well known in the pharmaceutical literature for producing fine drug particles in the micro or nanometer size range. These methods can be divided into three primary categories: (1) mechanical micronization (2) solution based phase separation and (3) rapid freezing techniques.

Mechanical micronization is most commonly done by milling techniques that can produce particles in the range of 1 to 20 microns. The most common processes utilized for this type of mechanical particle size reduction are ball and jet milling. Milling drug particles by these processes can reduce primary drug particles to micron-sized particles, however high surface energy results in aggregation of primary particles which to an extent negates the milling process. Nykamp et al. and Carstensen et al. demonstrated a melt grinding and jet milling technique to produce drug loaded microparticles of polylactic acid or polylactic-co-glycolic acid with mean particle size in the range of four to six microns (25, 26).

There are many solution based phase separation processes documented in the pharmaceutical literature for producing micro and nano-sized drug particles. Some of the more commonly known processes are spray drying, emulsification/evaporation, emulsification/solvent extraction, and complex coacervation. Some of the lesser-known processes are, for the sake of brevity, listed below along with their respective illustrating references: a) gas antisolvent precipitation (GAS)—(27) and WO9003782 EP0437451 EP0437451 DK59091; b) precipitation with a compressed antisolvent (PCA)—(28) and U.S. Pat. No. 5,874,029; c) aerosol solvent extraction system (ASES)—(29); d) evaporative precipitation into aqueous solution (EPAS)—(30) US patent application 20040067251; e) supercritical antisolvent (SAS)—(31); f) solution-enhanced dispersion by supercritical fluids (SEDS)—(32); g) rapid expansion from supercritical to aqueous solutions (RESAS)—(33); and h) anti-solvent precipitation.

Freezing techniques for producing micro or nano-sized drug particles are listed below along with their respective illustrating references: a) spray freezing into liquid (SFL)—(34) WO02060411 USPTO App. #2003054042 and 2003024424; and b) ultra rapid freezing (URF)—(35).

It should be noted that fine drug particles produced by solution-based phase separation or rapid freezing techniques are often amorphous in nature. Theses amorphous particles can be stabilized by complexation or coating during the production process with one or more excipient carriers having high melting points or glass transition temperatures. Stabilized amorphous fine drug particles can be formulated into the present preparation in the same manner as crystalline fine drug particles. The high shear of the hot-melt extrusion process will effectively deaggregate and disperse the amorphous drug particles (likely to be aggregated before extrusion due to high surface energy as stated in the next paragraph) into the stabilizing and non-solubilizing carrier thereby separating the aggregated particles into primary particles that are stabilized against aggregation and agglomeration on processing and storage by the carrier system. The excipient system with which the amorphous drug particles are complexed or coated will prevent recrystallization during hot-melt extrusion and storage of the amorphous drug-containing particle domains that are dispersed in the stabilizing and non-solubilizing carrier matrix. The benefit of this form of an amorphous dispersion compared to a traditional amorphous dispersion is that the formation of fine amorphous drug particles is not dependent on the solubility of the drug in the carrier system, since the amorphous drug particles are not formed in situ by the solubilization of the crystalline drug particles by the carrier system.

It has been reported that fine drug particles produced by processes such as those listed above exhibit high surface energy resulting in strong cohesive forces between particles. Zimon showed that powders of fine particles are likely to aggregate because the force of detachment is dependent on particle mass which is small in the case of fine particles (36). The forces of cohesion between individual fine particles are therefore greater than the forces of detachment, and thus particle aggregates form. French et al. demonstrated that the forces of cohesion between particles increase with decreasing particle size (37). Therefore, the extent of aggregation is increased as particle size is reduced.

Aggregation of fine particles results in an increase in the apparent particle size, consequently, particle size reduction is somewhat negated. In order to achieve the full benefit of particle size reduction, i.e. accelerated dissolution rate, aggregates must be reduced to individual particles when dosed. Lui and Stewart demonstrated a reduction in dissolution rate of benzodiazepines with an increasing extent of particle aggregation (38).

Particle agglomeration with storage also causes an increase in apparent particle size, and a corresponding decrease in dissolution rate. Ticehurst et al. demonstrated agglomeration of micronized revatropate hydrobromide when stored at greater than 25% relative humidity (39). Therefore, in the production of an ideal solid dosage form containing fine drug particles, aggregates would be separated and stabilized as individual particles by a carrier system during processing. The carrier system would also function to impede particle aggregation and agglomeration on storage at ambient and accelerated temperature and humidity conditions.

There have been few published reports of the successful incorporation of fine drug particles into a traditional dosage forms. Hu et al. developed an immediate release tablet of Danazol micronized powder by the SFL process, however only 5.3% drug loading was reported (40). Authors have also reported on the oral delivery of fine drug particles in the form of a stabilized liquid suspension (41, 42). There are two important limitations of delivering fine drug particle formulations in a liquid suspension, namely the instability of the preparation and the commercial limitation of shipping suspensions. Liquid suspensions are known to be unstable on storage due to agglomeration, and sedimentation, as well as caking of suspended particles. Commercially it is not ideal to formulate a pharmaceutical preparation as a suspension due to the cost of shipping the excess weight of the liquid vehicle, as compared to a solid dosage form.

Prior art examples such as those given above demonstrate the ongoing need for the advantageous properties of the present invention for the delivery of drug from a hot-melt extruded composition comprising fine drug particles.

SUMMARY OF THE INVENTION

The present invention seeks to overcome some or all of the disadvantages inherent in the above-mentioned compositions and methods. The present invention allows for high drug loading of fine drug particles in a stable and easily portable solid dosage form. In addition, the preparation can be formulated to provide a variety of drug release profiles to most sites of administration.

The present invention relates to pharmaceutical formulations comprised of active compounds finely and homogenously dispersed in one or more polymeric carriers that are produced by hot-melt extrusion techniques. Such preparations have been described as solid dispersions, glass solutions, molecular dispersions, and solid solutions.

The composition herein may be formulated to avoid the problem of phase separation with increasing concentration by incorporating into the carrier system crystalline fine drug particles or stabilized amorphous fine drug particles produced prior to extrusion. Additionally, by dispersing crystalline or stabilized, preformed amorphous fine drug particles into the non-solubilizing, stabilizing carrier system via the high shear extrusion process, problems of recrystallization of amorphous domains, as well as particle aggregation and agglomeration are overcome.

The present invention addresses the problem of physical instability of traditional solid dispersions and the resulting time-dependent drug release profile by dispersing, via hot-melt extrusion, fine drug particles in a thermodynamically stable crystalline state, or in a stabilized amorphous state into a polymeric carrier which will act to separate and isolate individual drug particles, thus preventing aggregation and agglomeration during processing and on storage. The carrier is formulated such that it will not substantially compromise the integrity of the individual drug particles during extrusion, such as by dissolving all or a significant part of the drug particles.

This invention also relates to the field of fine particle technology in that fine particles produced from any fine particle production technology can be incorporated into the claimed pharmaceutical preparation.

The present invention can be formulated to achieve an advantageous dosage form comprising fine drug particles. Processing powders of fine drug particles with a stabilizing and non-solubilizing carrier system by hot-melt extrusion one or more times reduces particle aggregation and stabilizes them as individual fine drug particles. The resulting product is a solid dispersion of fine particles stabilized by the carrier system, wherein the composition maintains primary particle integrity on storage.

One aspect of the invention provides a hot-melt extruded pharmaceutical composition comprising an effective amount of a therapeutic compound dispersed as fine particles in a stabilizing and non-solubilizing carrier system. The fine drug-containing particles are dispersed within the carrier system via hot-melt extrusion as discrete particles in a size range of less than one hundred microns, less than twenty microns, or less than five microns. A substantial majority, e.g. at least 75% wt., of the particles are not agglomerated or aggregated by the hot-melt extrusion process used to prepare the composition. In other words, at least 75% wt. of the particles are present in unagglomerated form.

Another aspect of the invention provides a method of preparing a hot-melt extruded pharmaceutical composition comprising fine drug-containing particles dispersed in a stabilizing and non-solubilizing thermally processable carrier, the method comprising the steps of:
providing a charge of fine drug-containing particles of a therapeutic compound;
providing a charge of stabilizing and non-solubilizing hot-melt extrudable carrier; and
mixing and hot-melting extruding the charges to form the hot-melt extruded pharmaceutical composition; wherein a substantial majority of the fine drug particles are not agglomerated or aggregated as a result of the step of hot-melt extruding.

The invention also provides a pharmaceutical solid dosage form having a stabilized release profile, the dosage form comprising a hot-melt extruded pharmaceutical composition comprising fine drug particles of a therapeutic compound dispersed in a stabilizing and non-solubilizing carrier.

In some embodiments, the stabilizing and non-solubilizing carrier is hot-melt extrudable meaning it can be hot-melt-extruded with no significant thermal degradation. The stabilizing and non-solubilizing carrier can also be thermally processable, meaning it softens and melts at the processing temperature with no significant thermal degradation. In some embodiments, a major portion of the stabilizing and non-solubilizing carrier is selected from the group consisting of polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxy ethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, sucrose stearate, xanthan gum, lipids, waxes, mono, di, and tri glycerides, cetyl alcohol, steryl alcohol. parafilm waxes and the like, hydrogenated vegetable and castor oil, glycerol monostearte, polyolefins including xylitol, mannitol, and Sorbitol, alpha hydroxyl acids including citric and tartaric acid edipic acid meleaic acid malic acid, citric acid, enteric polymers such as CAP, HPMC AS, shellac, and a combination thereof. The stabilizing and non-solubilizing carrier can further comprise surfactant carbohydrate, a high HLB surfactant, a low HLB surfactant, tablet excipient, filler, binder, disintegrant, super disintegrant, protein, peptide, enzyme, hormone, protein or a combination thereof. In some embodiments, the stabilizing and non-solubilizing carrier is selected from the group consisting of fixed oil, nonpolar vehicle, and water miscible ingredients including alcohols and glycols such as the PEGs (poly (ethylene glycol)) and PG (propylene glycol).

When provided as a pharmaceutical composition, the pharmaceutical composition (or dosage form) can provide an immediate or rapid release of therapeutic compound after exposure to an environment of use. Alternatively or additionally, the pharmaceutical composition (or dosage form) can be adapted to provide an extended release of therapeutic compound after exposure to an environment of use. Likewise, the pharmaceutical composition (or dosage form) can be adapted to provide a delayed release of therapeutic compound after exposure to an environment of use.

A dosage form containing the pharmaceutical composition can be selected from the group consisting of bead, tablet, pill, granulate, powder, capsule, tube, strand, cylinder, or film and can be further processed into a powder, pellets, or powder coatings for application on various substrates.

The pharmaceutical dosage form can be formulated, for example, for transdermal, transmucosal, rectal, pulmonary, nasal, vaginal, ocular, or otic drug delivery, or as an implantable drug delivery device.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

DETAILED DESCRIPTION OF THE INVENTION

Figure 1A:
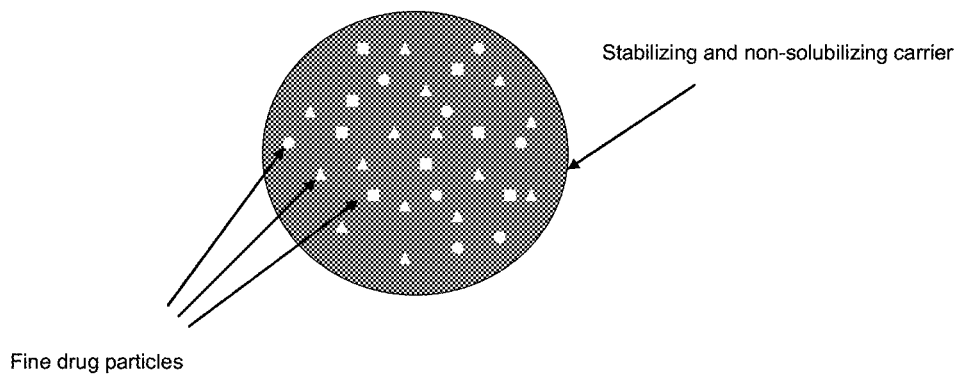
FIGS. 1a and b depict cross-sectional front elevation of an exemplary embodiment of a hot-melt extruded composition according the invention.

The drug-containing particles do not undergo substantial aggregation or agglomeration during hot-melt extrusion and/or can be deaggregated to essentially primary particles during hot-melt extrusion due to the intense mixing and agitation that occurs during the process. In some cases, the extrudate may need to be processed more than one time through the extruder in order to provide the desired degree of deaggregation. As used herein, the term "deaggregate", as used in reference to the drug-containing particles, means to reduce a loosely bound agglomerate to essentially its primary constituent particles. As used herein, the term "to agglomerate" or "agglomeration", as used in reference to the drug-containing particles means individual particles form a larger particle.

The fine drug-containing particles may be produced by one of many processes well known in the pharmaceutical literature. Such processes include mechanical milling by ball mill, jet mill, or other similar grinding process; solution based phase separation techniques such as spray drying, emulsification/evaporation, emulsification/solvent extraction, complex coacervation, anti-solvent precipitation, gas antisolvent precipitation (GAS), precipitation with a compressed antisolvent (PCA), aerosol solvent extraction system (ASES), evaporative precipitation into aqueous solution (EPAS), supercritical antisolvent (SAS), solution-enhanced dispersion by supercritical fluids (SEDS), rapid expansion from supercritical to aqueous solutions (RESAS), pressure induced phase separation (PIPS); or freezing techniques such as spray freezing into liquid (SFL) and ultra rapid freezing (URF). Detailed descriptions of these methods are included in references cited herein, the entire disclosures of which are hereby incorporated by reference.

Examples 6 and 7 below provide exemplary detailed procedures for the preparation of fine drug-containing particles by SFL and EPAS, respectively.

The drug-containing particles can comprise one or more drugs alone or a mixture of drug and one or more other adjunct stabilizers, such as sorbitan esters, polyoxyethylene sorbitan fatty acid esters, polyoxyethylene alkyl ethers, poloxamers (polyethylene-polypropylene glycol block copolymers), sucrose esters, sodium lauryl sulfate, oleic acid, lauric acid, vitamin E TPGS, polyoxyethylated glycolysed glycerides, dipalmitoyl phosphaditiyl choline, glycolic acid and salts, deoxycholic acid and salts, sodium fusidate, cyclodextrins, polyethylene glycols, polyglycolyzed glycerides, polyvinyl alcohols, polyacrylates, polymethacrylates, polyvinylpyrrolidones, phosphatidyl choline and derivatives, and cellulose derivatives. Excipients such as these can be used as adjunct stabilizers to complex or coat fine particles in-situ for particle stabilization and/or improved wetting.

If materials other than drug are present in the drug-containing particles, such materials can be present up to an amount of about or less than 90% wt., about or less than 50% wt., or about or less than 10% wt. of the weight of drug-containing particles present.

The drug present in the drug-containing particles can be crystalline or amorphous in form or a combination thereof. The form of the drug in the drug-containing particle does not change substantially during hot-melt extrusion. This means that the extent of crystallinity or amorphousness of the drug-containing particles remains substantially the same after processing as it was before processing. Specifically, less than about 5% by weight of a crystalline charge of drug-containing particles is made amorphous, and conversely less than about 5% by weight of an amorphous charge of drug-containing particles is made crystalline by hot-melt extrusion when such process is conducted as described herein.

The drug-containing particles typically have a mean particle diameter (based on the volume size distribution when approximated to a sphere) of about 100 microns or less, about 50 microns or less, about 10 microns or less, or about 1 micron or less. In some embodiments, the fine drug-containing particles will be stabilized in the nanometer range according to their method of preparation. Fine drug-containing particles produced by mechanical means typically range in size from 20 to 1 microns. Particles produced by solution-based phase separation or rapid freezing techniques typically have mean particle diameters ranging from 10 micrometers to 50 nanometers.

According to some embodiments of the invention, greater than 75% of the drug-containing particles have an average diameter of less than about 20 microns, 5 microns, or 1 micron depending on the method of preparation of the particles.

The loading of fine drug-containing particles in the hot-melt extruded preparation may be up to concentrations of 80%. The particles are deaggregated and homogenously dispersed as primary particles into a non-solubilizing, stabilizing carrier system owing to the high shear of the hot-melt extrusion process.

The nature of the carrier is such that the fine drug particles are not solubilized to a substantial degree in it during extrusion, i.e. the drug particles are practically insoluble in the carrier system at the extrusion temperature. The carrier also acts to stabilize the fine drug-containing particles such that particle aggregation or agglomeration does not occur, or only an insignificant amount, i.e., about 5% by number or less of the drug-containing particles, of aggregation or agglomeration does not occur, on processing, or upon storage at various temperature and relative humidity conditions. Therefore, 5% by number or less of the drug-containing particles are present in the composition in agglomerated form.

As used herein, the term "stabilizing and non-solubilizing carrier" refers to a material, or combination of materials, that is used as the matrix in which the drug-containing particles are dispersed during hot-melt extrusion. A stabilizing and non-solubilizing carrier does not solubilize, or solubilizes an insubstantial amount, e.g. about 10% wt. or less, of the drug-containing particles charged into the hot-melt extrusion apparatus. In addition, a stabilizing and non-solubilizing carrier stabilizes the average particle size of the fine drug particles by preventing or minimizing agglomeration and crystal growth on processing and storage.

The stabilizing and non-solubilizing carrier must be processable by hot-melt extrusion, meaning that the carrier must be able to melt and/or soften sufficiently to permit processing by hot-melt extrusion without substantial degradation of the carrier or the drug-containing particles. As such, the stabilizing and non-solubilizing carrier can include a thermal binder, a pressure softenable binder, or a combination thereof.

Exemplary thermal binders include: polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxy ethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, and xanthan gum. One embodiment of the binder is poly(ethylene oxide) (PEO), which can be purchased commercially from companies such as the Dow Chemical Company, which markets PEO under the POLY OX™ trademark exemplary grades of which can include WSR N80 having an average molecular weight of about 200,000; 1,000,000; and 2,000,000.

Suitable grades of PEO can also be characterized by viscosity of solutions containing fixed concentrations of PEO, such as for example:

| POLYOX Water-Soluble Resin NF | Viscosity Range Aqueous Solution at 25° C., mPa · s |
|---|---|
| POLYOX Water-Soluble Resin NF WSR N-10 | 30-50 (5% solution) |
| POLYOX Water-Soluble Resin NF WSR N-80 | 55-90 (5% solution) |
| POLYOX Water-Soluble Resin NF WSR N-750 | 600-1,200 (5% solution) |

| POLYOX Water-Soluble Resin NF | Viscosity Range Aqueous Solution at 25° C., mPa · s |
|---|---|
| POLYOX Water-Soluble Resin NF WSR-205 | 4,500-8,800 (5% solution) |
| POLYOX Water-Soluble Resin NF WSR-1105 | 8,800-17,600 (5% solution) |
| POLYOX Water-Soluble Resin NF WSR N-12K | 400-800 (2% solution) |
| POLYOX Water-Soluble Resin NF WSR N-60K | 2,000-4,000 (2% solution) |
| POLYOX Water-Soluble Resin NF WSR-301 | 1,650-5,500 (1% solution) |
| POLYOX Water-Soluble Resin NF WSR Coagulant | 5,500-7,500 (1% solution) |
| POLYOX Water-Soluble Resin NF WSR-303 | 7,500-10,000 (1% solution) |

Suitable thermal binders that may or may not require a plasticizer include, for example, EUDRAGIT™ RS PO, EUDRAGIT™ S100, Kollidon SR (poly(vinyl acetate)-co-poly(vinylpyrrolidone) copolymer), ETHOCEL™ (ethylcellulose), HPC (hydroxypropylcellulose), cellulose acetate butyrate, poly(vinylpyrrolidone) (PVP), poly(ethylene glycol) (PEG), poly(ethylene oxide) (PEO), poly(vinyl alcohol) (PVA), hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.), cellulose acetate phthalate (CAP), cellulose acetate trimelletate (CAT), poly(vinyl acetate) phthalate (PVAP), hydroxypropylmethylcellulose phthalate (HPMCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, EUDRAGIT L-30-D™ (MA-EA, 1:1), EUDRAGIT L-100-55™ (MA-EA, 1:1), hydroxypropylmethylcellulose acetate succinate (HPMCAS), COATERIC™ (PVAP), AQUATERIC™ (CAP), and AQUACOAT™ (HPMCAS), polycaprolactone, starches, pectins; polysaccharides such as tragacanth, gum arabic, guar gum, and xanthan gum.

The stabilizing and non-solubilizing carrier may also contain various functional excipients, such as: hydrophilic polymer, antioxidant, super-disintegrant, surfactant including amphiphilic molecules, wetting agent, stabilizing agent, retardant, similar functional excipient, or combination thereof, and plasticizers including citrate esters, polyethylene glycols, PG, triacetin, diethylphthalate, castor oil, and others known to those or ordinary skill in the art. Extruded material may also include acidifying agent, adsorbent, alkalizing agent, buffering agent, colorant, flavorant, sweetening agent, diluent, opaquant, complexing agent, fragrance, preservative or a combination thereof.

Exemplary hydrophilic polymers which can be a primary or secondary polymeric carrier that can be included in the composition include poly(vinyl alcohol) (PVA), polyethylene-polypropylene glycol (e.g. POLOXAMER™), carbomer, polycarbophil, or chitosan. The "hydrophilic polymers" of the present invention include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan, and povidone. "Hydrophilic polymers" also include polyethylene oxide, sodium carboxymethylcellulose, hydroxyethyl methyl cellulose, hydroxymethyl cellulose, carboxypolymethylene, polyethylene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

As used herein, the term "antioxidant" is intended to mean an agent that inhibits oxidation and thus is used to prevent the deterioration of preparations by oxidation due to the presence of oxygen free radicals or free metals in the composition. Such compounds include, by way of example and without limitation, ascorbic acid, ascorbyl palmitate, butylated hydroxyanisole, butylated hydroxytoluene, hypophosphorous acid, monothioglycerol, sodium ascorbate, sodium formaldehyde sulfoxylate and sodium metabisulfite and others known to those of ordinary skill in the art. Other suitable antioxidants include, for example, vitamin C, BHT, BHA, sodium bisulfite, vitamin E and its derivatives, propyl gallate or a sulfite derivative.

As used herein, the term "disintegrant" is intended to mean a compound used in solid dosage forms to promote the disruption of a solid mass (layer) into smaller particles that are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g., Avicel™), carboxymethylcellulose calcium, croscarmellose sodium, alginic acid, sodium alginate, cellulose polyacrilin potassium (e.g., AMBERLITE™), alginates, sodium starch glycolate, gums, agar, guar, locust bean, karaya, pectin, tragacanth, crospovidone and other materials known to one of ordinary skill in the art. A superdisintegrant is a rapidly acting disintegrant. Exemplary superdisintegrants include crospovidone and low substituted HPC.

Suitable surfactants include Polysorbate 80, sorbitan monooleate, sodium lauryl sulfate or others. Soaps and synthetic detergents may be employed as surfactants. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

Wetting agent is an agent that decreases the surface tension of a liquid. Wetting agents would include alcohols, glycerin, proteins, peptides water miscible solvents such as glycols, hydrophilic polymers Polysorbate 80, sorbitan monooleate, sodium lauryl sulfate, fatty acid alkali metal, ammonium, and triethanolamine salts, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

For the purpose of the present invention, stabilizing agents are polymers and excipients that do not solubilize the drug particles preferably agents with high melting points or glass transition temperatures and/or agents with no or minimal affinity for the active. The excipients restrict the mobility of drug particles within the carrier thereby reducing particle aggregation and agglomeration on processing and storage. Such excipients include cellulosic polymers including HPMC, HPC, methylcellulose; polyvinyl alcohol, polyvinylpyrrolidone, polyvinylpyrrolidone-co-vinyl acetate and others known to those of ordinary skill in the art.

Retardants are agents that are insoluble or slightly soluble polymers with a Tg above 45° C., more preferably above 50° C. before being plasticized by other agents in the formulation including other polymers and other excipients needed for processing. The excipients include waxes, acrylics, cellulosics, lipids, proteins, glycols, and the like.

Under the conditions of the hot-melt extrusion process of the invention, the fine drug-containing particles are deaggregated and homogenously dispersed such that they exist within the carrier as individual particles having a median particle diameter size range of less than one hundred microns, or less than twenty microns, and or less than five microns. The extrusion process may be performed once, or several times in series to further deaggregate and disperse the drug particles.

The resulting product can be produced in the form of tubes, strands, cylinders, or films; and can be further processed to fine powders, granules, pellets, spheres, or tablets that are intended for oral delivery. The resulting product can also be formulated for transdermal, transmucosal, rectal, pulmonary, nasal, vaginal, ocular, or otic drug delivery as well as an implantable drug delivery device.

The solid dosage formulations of the invention can assume any shape or form known in the art of pharmaceutical sciences. The dosage form can be a sphere, tablet, bar, plate, paraboloid of revolution, ellipsoid of revolution or other one known to those of ordinary skill in the art. The solid dosage form can also include surface markings, cuttings, grooves, letters and/or numerals for the purposes of decoration, identification and/or other purposes.

The resulting composition is characterized by the substantial absence of agglomerated or aggregated fine drug-containing particles after processing and after storage for extended times and at various temperature and humidity conditions.

The carrier and/or the additional functional excipients may be formulated as to provide a predetermined approximate release profile under predetermined conditions. The drug can be released according to an immediate, fast melt, rapid, sustained, controlled, slow, pulsatile or extended, and optionally delayed, targeted or timed drug release profile. The pharmaceutical composition may deliver one or more active agents in an extended release manner, and mechanisms employed for such delivery can include active agent release that is pH-dependent or pH-independent; diffusion or dissolution controlled; pseudo-zero order (approximates zero-order release), zero-order, pseudo-first order (approximates first-order release), or first-order; or slow, delayed, timed or sustained release or otherwise controlled release. The release profile for the active agent can also be sigmoidal in shape, wherein the release profile comprises an initial slow release rate, followed by a middle faster release rate and a final slow release rate of active agent.

By "immediate release" is meant a release of an active agent to an environment over a period of seconds to no more than about 30 minutes once release has begun and release begins within no more than about 2 minutes after administration. An immediate release does not exhibit a significant delay in the release of drug.

By "rapid release" is meant a release of an active agent to an environment over a period of 1-59 minutes or 0.1 minute to three hours once release has begun and release can begin within a few minutes after administration or after expiration of a delay period (lag time) after administration.

As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. An extended release tablet generally effects at least a two-fold reduction in dosing frequency as compared to the drug presented in a conventional dosage form (e.g., a solution or rapid releasing conventional solid dosage forms).

By "controlled release" is meant a release of an active agent to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered. The term "controlled release", as regards to drug release, includes the terms "extended release", "prolonged release", "sustained release", or "slow release", as these terms are used in the pharmaceutical sciences. An controlled release can begin within a few minutes after administration or after expiration of a delay period (lag time) after administration.

A slow release dosage form is one that provides a slow rate of release of drug so that drug is released slowly and approximately continuously over a period of 3 hr, 6 hr, 12 hr, 18 hr, a day, 2 or more days, a week, or 2 or more weeks, for example.

A timed release dosage form is one that begins to release drug after a predetermined period of time as measured from the moment of initial exposure to the environment of use.

A targeted release dosage form generally refers to an oral dosage form that designed to deliver drug to a particular portion of the gastrointestinal tract of a subject. An exemplary targeted dosage form is an enteric dosage form that delivers a drug into the middle to lower intestinal tract but not into the stomach or mouth of the subject. Other targeted dosage forms can delivery to other sections of the gastrointestinal tract such as the stomach, jejunum, ileum, duodenum, cecum, large intestine, small intestine, colon, or rectum.

By "delayed release" is meant that initial release of drug occurs after expiration of an approximate delay (or lag) period. For example, if release of drug from an extended release composition is delayed two hours, then release of drug from begins at about two hours after administration of the composition, or dosage form, to a subject. In general, a delayed release is opposite an immediate release, wherein release of drug begins after no more than a few minutes after administration. Accordingly, the drug release profile from a particular composition can be a delayed-extended release or a delayed-rapid release. A "delayed-extended" release profile is one wherein extended release of drug begins after expiration of an initial delay period. A "delayed-rapid" release profile is one wherein rapid release of drug begins after expiration of an initial delay period.

A pulsatile release dosage form is one that provides pulses of high active ingredient concentration, interspersed with low concentration troughs. A pulsatile profile containing two peaks may be described as "bimodal".

A pseudo-first order release profile is one that approximates a first order release profile. A first order release profile characterizes the release profile of a dosage form that releases a constant percentage of an initial drug charge per unit time.

A pseudo-zero order release profile is one that approximates a zero-order release profile. A zero-order release profile characterizes the release profile of a dosage form that releases a constant amount of drug per unit time.

The resulting product may also be formulated to exhibit enhanced dissolution rate of a formulated poorly water soluble drug.

Due to the deaggregation of fine particles on processing to form primary particles that are stabilized by the carrier system, the composition or dosage form will generally possess a substantially stable release profile during storage. As used herein, the term "stable release profile" refers to a dosage form that provides approximately the same release profile for a drug over the period of time during which the dosage form is stored. More specifically, a stable release profile is one wherein a dosage form provides a first release profile after being stored a short first period of time under a first set of conditions and provides a second release profile after being stored a longer second period of time under the same first set of conditions such that the first and second release profiles vary by no more than ±10%. Therefore, an unstable release profile is one wherein the first and second release profiles are not approximately the same, i.e. vary by more than ±10%.

An example of a composition or formulation having a stable release profile follows. Two tablets having the same formulation are made. The first tablet is stored for one day under a first set of conditions, and the second tablet is stored for four months under the same first set of conditions. The release profile of the first tablet is determined after the single day of storage and the release profile of the second tablet is determined after the four months of storage. If the release profile of the first tablet is approximately the same as the release profile of the second tablet, then the tablet/film formulation is considered to have a stable release profile.

Another example of a composition or formulation having a stable release profile follows. Tablets A and B, each comprising a film composition according to the invention, are made, and Tablets C and D, each comprising a film composition not according to the invention, are made. Tablets A and C are each stored for one day under a first set of conditions, and tablets B and D are each stored for three months under the same first set of conditions. The release profile for each of tablets A and C is determined after the single day of storage and designated release profiles A and C, respectively. The release profile for each of tablet B and D is determined after the three months of storage and designated release profiles B and D, respectively. The differences between release profiles A and B are quantified as are the differences between release profiles C and D. If the difference between the release profiles A and B is less than the difference between the release profiles C and D, tablets A and B are understood to provide a stable or more stable release profile.

Figure 1B:
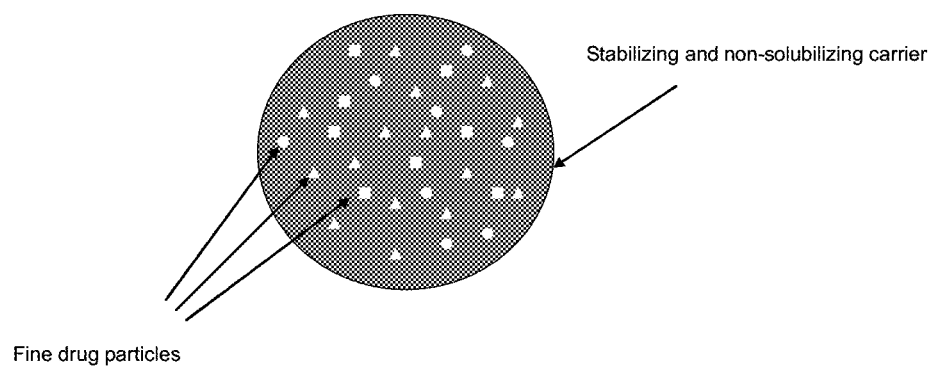

FIG. 1a depicts a conceptual cross-sectional front elevation of an exemplary hot-melt extruded composition according to the invention illustrating individualized fine drug particles homogenously dispersed in a stabilizing and non-solubilizing carrier system. FIG. 1b illustrates the same formulation after storage in sealed containers at 40° C. and 75% relative humidity. This figure represents the prevention or inhibition of particle aggregation or agglomeration on storage by the stabilizing carrier.

Visual inspection of exemplary compositions No. 1-No. 10 (Example 1) of the invention is conducted by SEM according to Example 2 or with the unaided eye. Some of the results are summarized below. Visual inspection of the composition of the invention was conducted by SEM and the unaided eye.

| No. | Transparency | Surface Texture | Color |
|---|---|---|---|
| 1 | Transparent | Smooth | Yellow |
| 2 | Opaque | Slightly textured | White |
| 3 | Translucent | Textured | Light yellow |
| 4 | Opaque | Textured | White |
| 5 | Translucent to opaque | Coarse | Light Yellow |
| 6 | Opaque | Coarse | White |
| 7 | Opaque | Smooth | White |
| 8 | Opaque | Slightly textured | White |
| 9 | Transparent | Smooth | Yellow |
| 10 | Opaque | Slightly textured | White |

The opaque and white appearance of extrudates containing itraconazole signifies that itraconazole is not solubilized by the carrier system when hot-melt extruded at 100° C. Being that this opacity was seen for each formulation, it can be concluded that each of the functional additives did not influence the solubility of itraconazole in PEO. For each of the other non-active formulations, the color and texture was seen to be homogenous, indicating that each of the additives are compatible with PEO when hot-melt extruded at 100° C. The appearance of a non-homogeneous color distribution or surface texture would generally signify aggregation and indicate immiscibility of the additive with PEO.

Figure 2A:
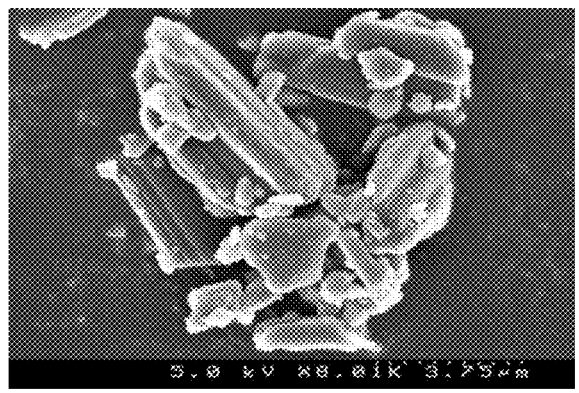
FIGS. 2a-2c, 3a-3c, 4a-4c, 5a-5c and 6a-6c depict electron micrographs of control and exemplary sample formulations prepared as described herein.
Figure 2B:
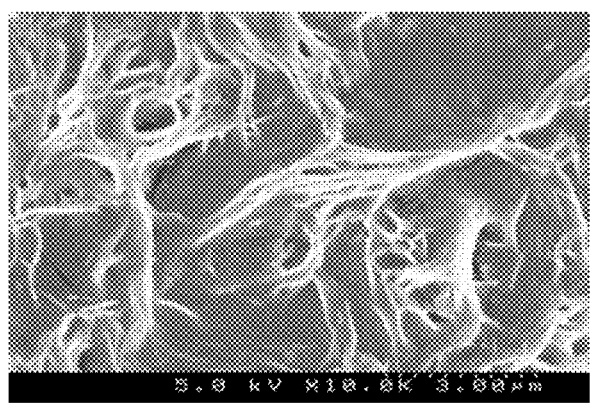
Figure 2C:
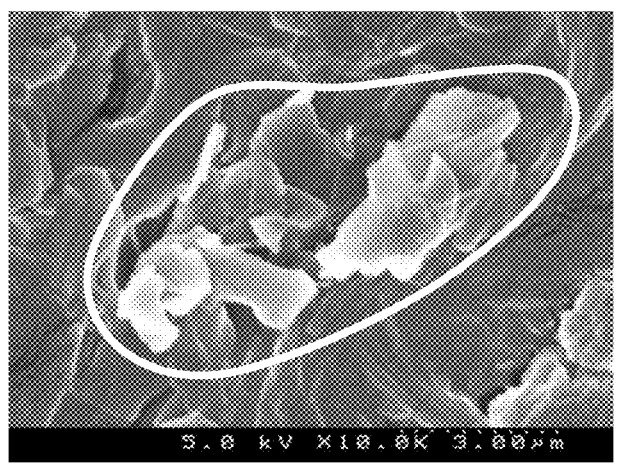

FIGS. 2a-2c depict SEM micrographs of micronized itraconazole (ITZ) (FIG. 2a) having an average particle size of 2.5 microns, hot-melt extruded PEO (FIG. 2b) having an average molecular weight of about 200,000, and hot-melt extruded formulation No. 2 (FIG. 2c). Initially, the ITZ shows some aggregation and/or agglomeration prior to hot-melt extrusion. However, during hot-melt extrusion the particles are deagglomerated and/or deaggregated and not dissolved by the carrier.

Figure 2D:
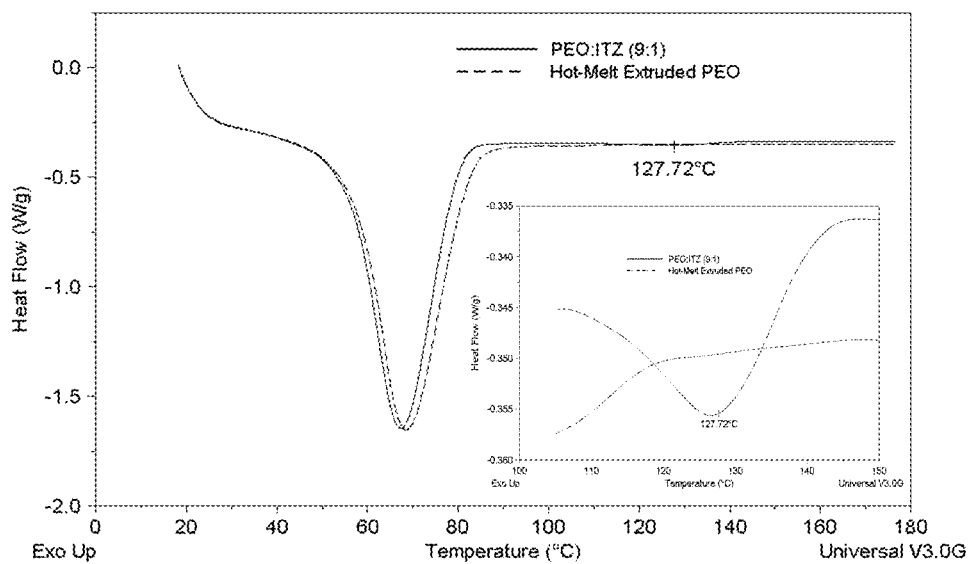
FIGS. 2d, 3d, 4d, 5d, and 6d depict DSC thermograms for control and exemplary sample formulations prepared as described herein.

FIG. 2d depicts a DSC thermogram for hot-melt extruded PEO and a composition made according to formula No. 2. The melting point of crystalline itraconazole is known to be about 165° C. The drug-containing composition shows a melting point of 127.72° C. for ITZ, signifying the temperature at which crystalline itraconazole is solubilized in PEO. This indicates that ITZ is present in its crystalline form in the extrudate, and it therefore is not solubilized by PEO when hot-melt extruded at 100° C. It is thus shown that PEO is a suitable thermal binder for a stabilizing and non-solubilizing carrier system for fine particles of itraconazole when hot-melt extruded at 100° C.

Figure 3A:
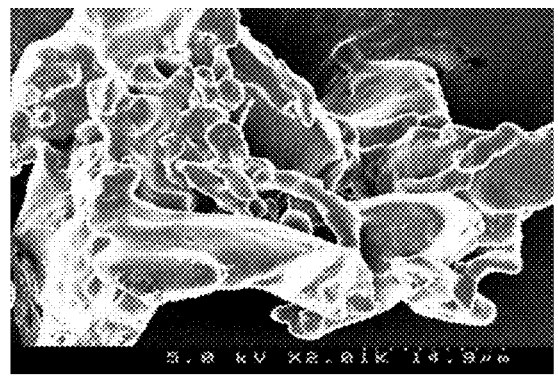
Figure 3B:
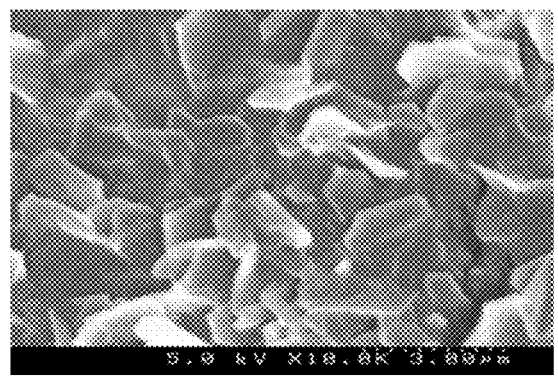
Figure 3C:
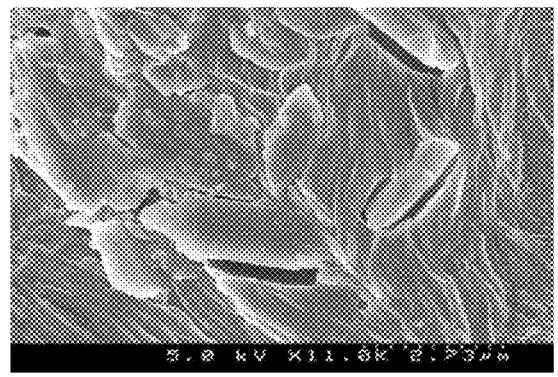

FIGS. 3a-3c depict SEM micrographs of HPMC E15 (FIG. 3a) having an average viscosity of 5 cPs as a 2% w solution with water, hot-melt extruded PEO and HPMC (FIG. 3b) according to formula No. 3, and hot-melt extruded formulation No. 4 (FIG. 3c). It is shown in FIG. 3b that HPMC is reduced in particle size and dispersed in a crystalline form throughout the PEO matrix indicating the miscibility of HPMC with PEO when hot-melt extruded at 100° C. When the ITZ is added, the extrudate now comprises readily identifiable particles of ITZ indicating that it is deaggregated during hot-melt extrusion and that the HPMC/PEO carrier does not solubilize the ITZ during extrusion. In fact, the particles are deagglomerated and/or deaggregated by the carrier during hot-melt extrusion.

Figure 3D:
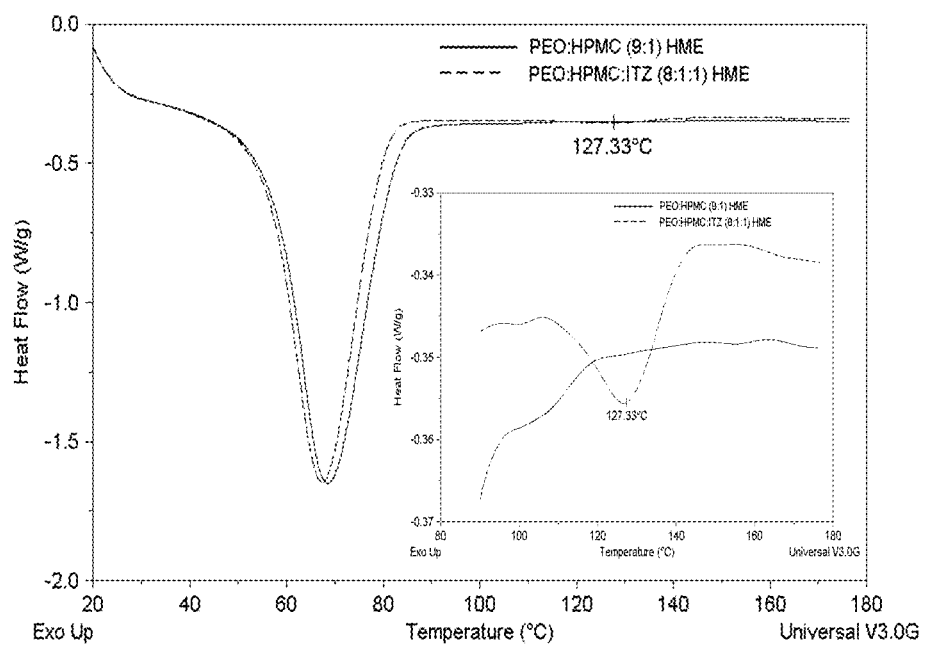

FIG. 3d includes a DSC thermogram for the formulations of FIGS. 3b and 3c. The drug-containing composition shows a melting point of 127.33° C. for ITZ meaning that ITZ is present in its crystalline form in the extrudate. This further demonstrates that ITZ is not solubilized by the PEO/HPMC carrier.

Figure 4A:
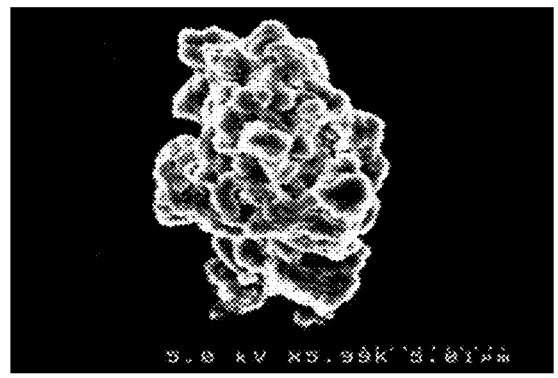
Figure 4B:
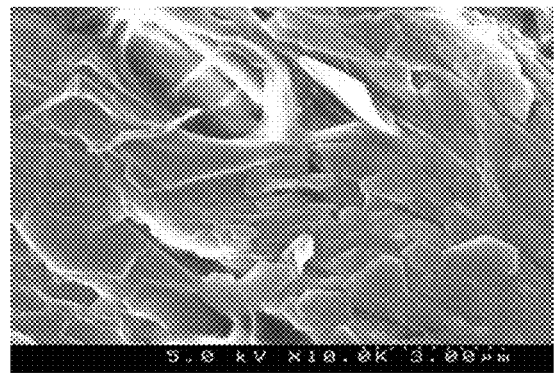
Figure 4C:
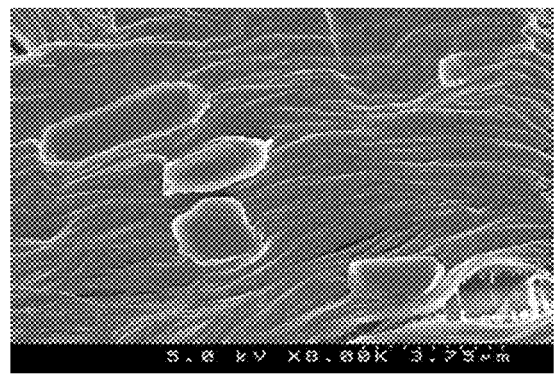

FIGS. 4a-4c depict SEM micrographs of PVA (FIG. 4a) having an average molecular weight of about 30 to 200,000 g/mol, hot-melt extruded PEO and PVA (FIG. 4b) according to Formulation No. 5, and hot-melt extruded formulation No. 6 (FIG. 4c). It is shown in FIG. 4b that HPMC is reduced in particle size and dispersed in a crystalline form throughout the PEO matrix indicating the miscibility of PVA with PEO when hot-melt extruded at 100° C. When the ITZ is added, the extrudate now comprises readily identifiable particles of ITZ indicating that it is deaggregated during hot-melt extrusion and not solubilized by the PEO/PVA carrier during extrusion. As above, the particles are deagglomerated and/or deaggregated by the carrier during hot-melt extrusion.

Figure 4D:
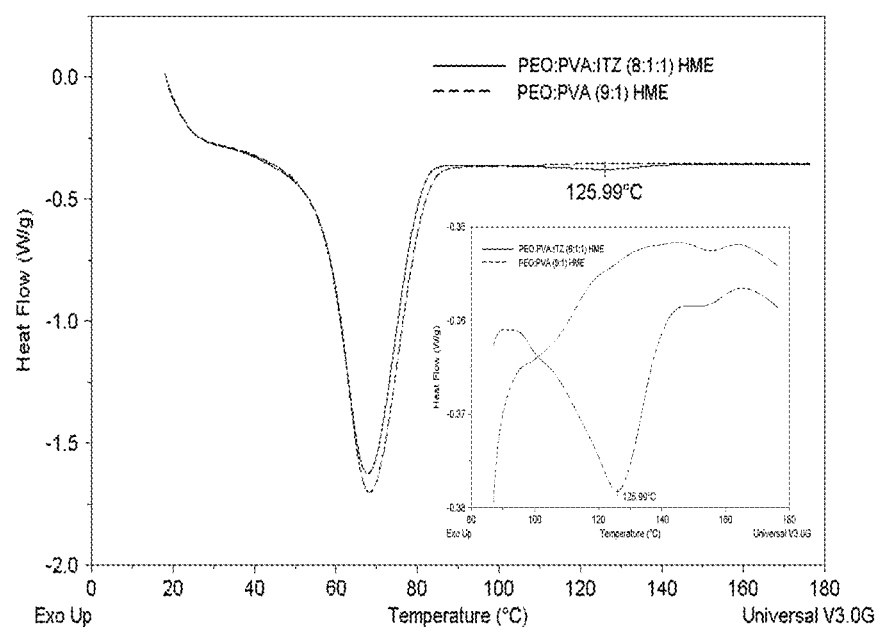

FIG. 4d includes a DSC thermogram for formulations of FIGS. 4b and 4c. The drug-containing composition shows a melting point of 125.99° C. for ITZ, again indicating that ITZ is present in its crystalline form in the extrudate and is therefore not solubilized by the carrier system. The slight depression of the melting point indicates that a small portion of the crystalline ITZ is solubilized by the carrier system below 127° C. A majority of this amount of dissolved ITZ is solubilized in a narrow temperature range near the solubilization point in this carrier system (125.99° C.). Therefore, it can be concluded that only a negligible amount, i.e less than 5% by wt. of the loaded ITZ is solubilized by the PVA in the formulation during hot-melt extrusion at 100° C. Increasing the ratio of PVA to ITZ above one to one may cause a greater extent of ITZ to become solubilized in the carrier system.

Figure 5A:
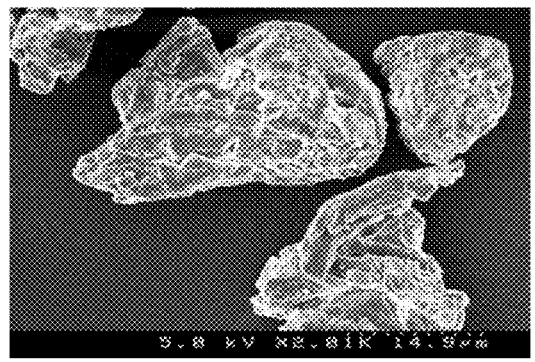
Figure 5B:
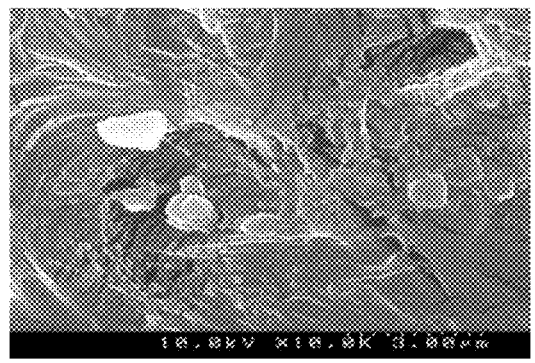
Figure 5C:
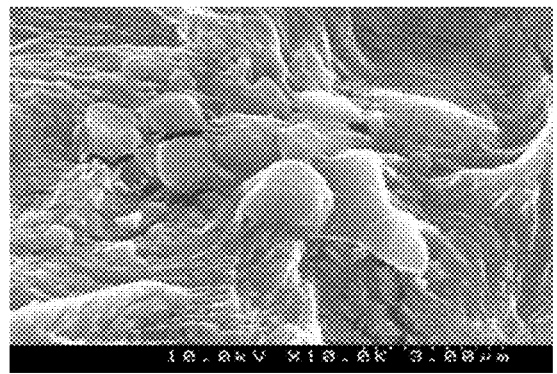

FIGS. 5a-5c depict SEM micrographs of sodium lauryl sulfate (SLS) (FIG. 5a), hot-melt extruded PEO and SLS (FIG. 5b) according to Formulation No. 7, and hot-melt extruded formulation No. 8 (FIG. 5c). It is shown in FIG. 5b that SLS is reduced in particle size and dispersed throughout the PEO matrix indicating the miscibility of SLS with PEO when hot-melt extruded at 100° C. When the ITZ is added, the extrudate now comprises readily identifiable particles of ITZ indicating that it is deaggregated during hot-melt extrusion and the PEO/SLS carrier does not solubilize the ITZ during extrusion. Again, the particles are deagglomerated and/or deaggregated by the carrier during hot-melt extrusion.

Figure 5D:
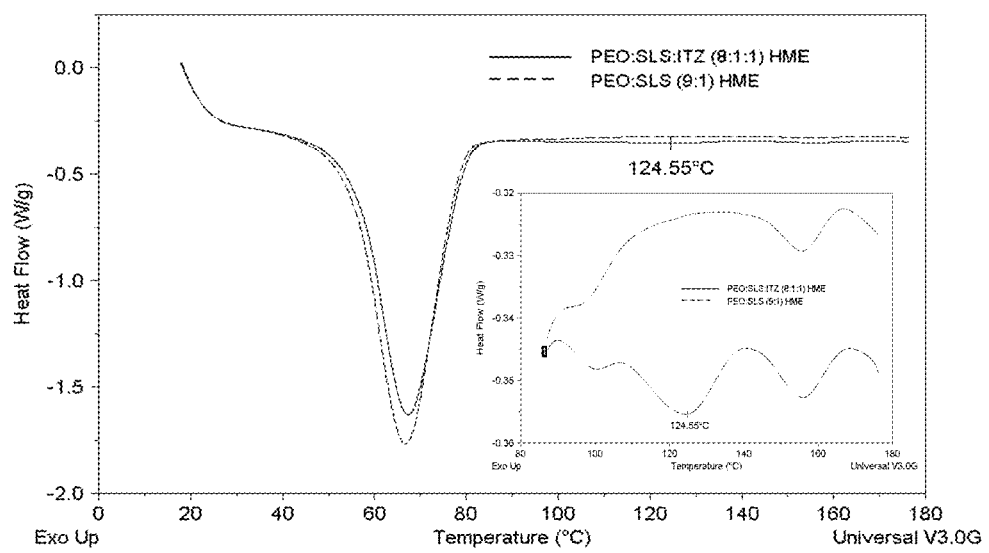

FIG. 5d includes a DSC thermogram for formulations of FIGS. 5b and 5c. The drug-containing composition shows a melting point of 124.55° C. for ITZ, again indicating that ITZ is present in its crystalline form in the extrudate and is therefore not solubilized by the carrier system. The slight depression of the melting point indicates that a small portion of the crystalline ITZ is solubilized by the carrier system below 127° C. Most of this amount of dissolved ITZ is solubilized in a narrow temperature range near the solubilization point in this carrier system (124.55° C.). Therefore, it can be concluded that only a negligible amount, i.e less than 5% by wt. of the loaded ITZ is solubilized by the SLS in the formulation during hot-melt extrusion at 100° C. Accordingly, embodiments of the invention wherein the carrier phase includes one or more components that solubilize a portion of the drug hot-melt extrusion include those components in amounts insufficient to solubilize a substantial amount of the drug during hot-melt extrusion. For example, such components are present in an amount such that less than 10% by wt., less than 5% by wt. or less than 1% by wt. of the drug can solubilize during hot-melt extrusion.

Figure 6A:
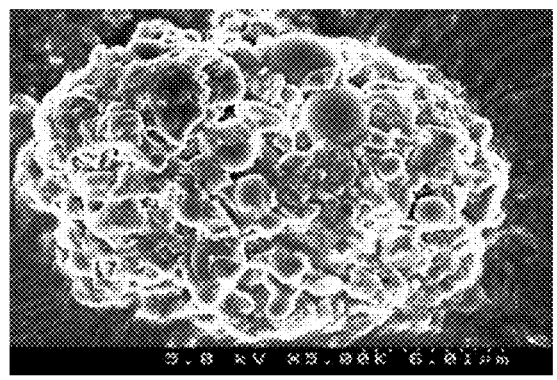
Figure 6B:
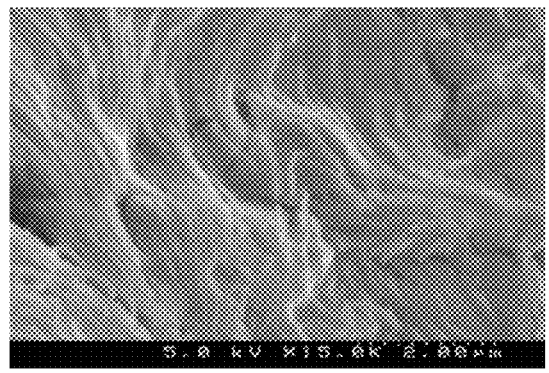
Figure 6C:
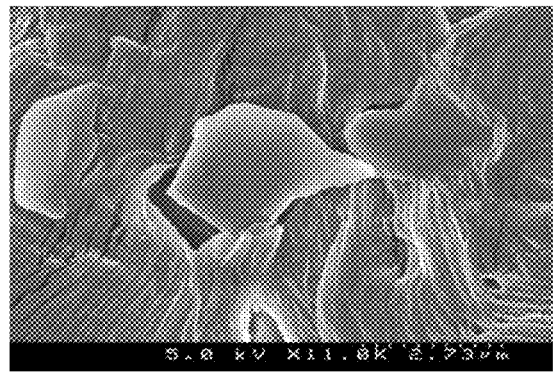

FIGS. 6a-6c depict SEM micrographs of poloxamer 407 (FIG. 6a) having an average molecular weight of about 9,840 to 14,600 g/mol, hot-melt extruded PEO and poloxamer (FIG. 6b) according to Formulation No. 9, and hot-melt extruded formulation No. 10 (FIG. 6c). The poloxamer and PEO form a substantially homogeneous extrudate indicating complete miscibility when hot-melt extruded at 100° C. When the ITZ is added, the extrudate now comprises readily identifiable particles of ITZ indicating that it is deaggregated during hot-melt extrusion and the PEO/poloxamer carrier does not solubilize the ITZ during extrusion. Again, the particles are deagglomerated and/or deaggregated by the carrier during hot-melt extrusion.

Figure 6D:
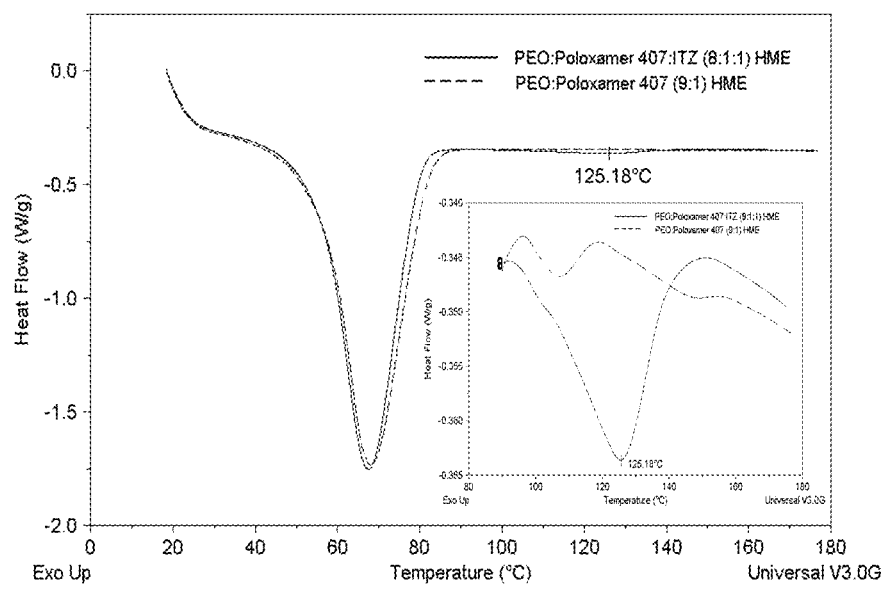

FIG. 6d includes a DSC thermogram for formulations of FIGS. 6b and 6c. The drug-containing composition shows a melting point of 124.18° C. for ITZ, again indicating that ITZ is present in its crystalline form in the extrudate, and is therefore not solubilized by the carrier system. The slight depression of the melting point indicates that a small portion of the crystalline ITZ is solubilized by the carrier system below 127° C. Most of this amount of dissolved ITZ is solubilized in a narrow temperature range near the solubilization point in this carrier system (124.18° C.). Therefore, it can be concluded that only a negligible amount, i.e less than 5 w of the loaded ITZ is solubilized by the poloxamer in the formulation during hot-melt extrusion at 100° C.

The above-described results indicate that the hot-melt extrudates composed of PEO and poloxamer formed a homogeneous polymer matrix when melt extruded at 100° C. Further, compositions containing HPMC, PVA, or SLS were observed to have homogenously dispersed particles throughout the PEO matrix following melt extrusion.

Upon visual inspection it was determined that the addition of itraconazole to each of the formulations produced opaque extrudates when melt extruded at 100° C. SEM revealed that crystalline itraconazole was dispersed as discrete particles throughout the polymeric matrix following extrusion for each composition.

DSC analysis of the compositions indicated that, at a loading of 10% (w/w), itraconazole it has a melting point of approximately 127° C. after melt extrusion with PEO at 100° C. Moreover, approximately the same melting point for itraconazole was also observed when any one of the chosen polymers or surfactants was incorporated into the extruded formulation.

Under the conditions evaluated, itraconazole is substantially insoluble in PEO when extruded at 100° C. as confirmed by SEM and DSC. In addition, the solubility of itraconazole in PEO when melt extruded at 100° C. was not influenced by the inclusion of HPMC, Poloxamer 407, PVA, or SLS to the formulation.

Figure 7:
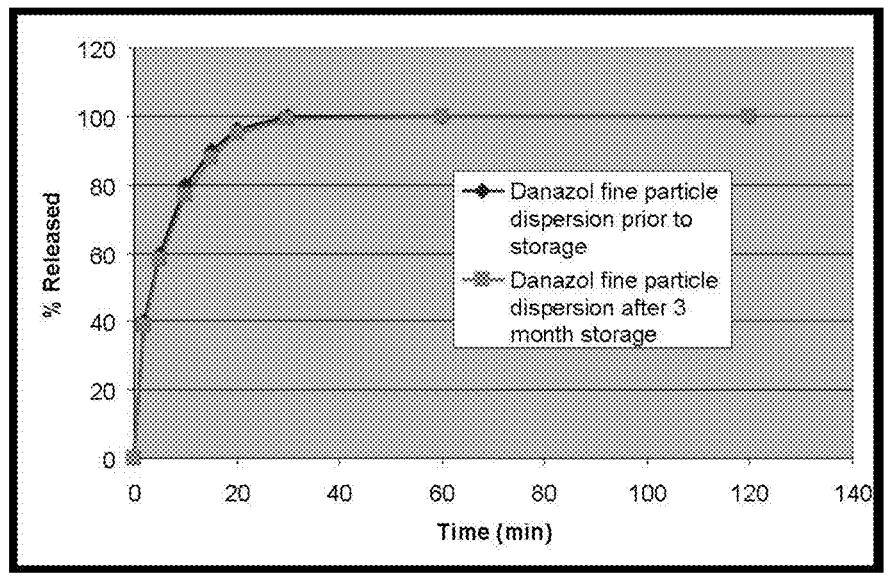
FIGS. 7-8 depict comparative drug release profiles for compositions of the invention before and after storage and drug release profiles for a composition not made according to the invention.

The ability of the carrier to provide a substantially stable release profile after storage of a composition according to the invention was determined by conducting dissolution profile assays for various controls and sample. FIG. 7 depicts exemplary drug release profiles for the composition of Example 1. The first line (diamond markers) depicts the release profile for danazol within one day of preparation of the composition. The second line (square markers) depicts the release profile for danazol following 3 months storage in sealed containers at 40° C. and 75% relative humidity. The drug release profile remains substantially the same.

The term "hot-melt extrusion" is used herein to describe a process whereby an excipient blend is heated to a molten state and subsequently forced through an orifice where the extruded product is formed into its final shape in which it is solidified upon cooling. The blend is conveyed through various heating zones typically by a screw mechanism. The screw or screws are rotated by a variable speed motor inside a cylindrical barrel where only a small gap exists between the outside diameter of the screw and the inside diameter of the barrel. In this conformation, high shear is created at the barrel wall and between the screw fights by which the various components of the powder blend are well mixed and deaggregated. The hot-melt extrusion equipment is typically a single or twin-screw apparatus, but can be composed of more than two screw elements. A typical hot-melt extrusion apparatus contains a mixing/conveying zone, a heating/melting zone, and a pumping zone in succession up to the orifice. In the mixing/conveying zone, the powder blends are mixed and aggregates are reduced to primary particles by the shear force between the screw elements and the barrel. In the heating/melting zone, the temperature is at or above the melting point or glass transition temperature of the thermal binder or binders in the blend such that the conveying solids become molten as they pass through the zone. A thermal binder in this context describes an inert excipient, typically a polymer, that is sufficiently solid at ambient temperature, but becomes molten or semi-liquid when exposed to elevated heat or pressure. The thermal binder acts as the matrix in which the active or actives and other functional ingredients are dispersed, or the adhesive with which they are bound such that a continuous composite is formed at the outlet orifice. Once in a molten state, the homogenized blend is pumped to the orifice through another heating zone that maintains the molten state of the blend. At the orifice, the molten blend can be formed into strands, cylinders or films. The extrudate that exits is then solidified typically by an air-cooling cooling process. Once solidified, the extrudate may then be further processed to form pellets, spheres, fine powder, tablets, and the like. An example of a single screw apparatus similar to the description above is the Randcastle Microtruder, model RCP-0750.

For the proposed invention, the active substance or substances include fine drug particles that are produced by a mechanical milling, a solvent based phase separation, or a rapid freezing process. These fine particles will enter the feeding zone of the extruder as aggregated particles due to strong interparticle cohesive forces. These fine particles will be deaggregated and dispersed in the carrier system by the high shear forces that exist between the screw elements and the barrel. Thus, the process serves as a means of reducing fine particle aggregates to primary particles such that the full benefit of particle size reduction is realized.

Temperature is an important process variable to consider for the proposed invention. To maintain the integrity of the fine drug particles, the blend is extruded at least ten degrees Celsius or more below the temperature at which the active substance dissolves into the carrier at the extruded ratio. For example, itraconazole is solubilized by PEO at approximately 127° C. in a nine to one ratio of PEO to itraconazole. Therefore, when extruding fine particles of itraconazole in a PEO carrier at a nine to one ratio, the greatest extrusion temperature must be at most 117° C. For amorphous fine drug particles, this maximum extrusion temperature is the temperature at which the stabilizing excipients become labile to an extent that recrystallization of the drug occurs. Therefore, it is important to formulate amorphous drug particles to include such excipients as polymers with high glass transition temperatures so that the maximum extrusion temperature is in a range above the softening temperatures of common thermal binders. Thus, the temperature at which the active compound dissolves into a carrier formulation or at which amorphous fine drug particles begin to recrystallize must be determined experimentally before deciding the most appropriate extrusion conditions. This can be done by DSC analysis for varying ratios of active particles to carrier and noting the temperature of the thermal event associated with the drug, i.e. the endothermic event for the melting point of crystalline drug and the exothermic event for the recrystallization of amorphous drug. When extruding compositions containing amorphous drug particles, the maximum extrusion temperature must be below the temperature of recrystallization, approximately 10° to 20° C. When extruding compositions containing crystalline drug particles, the maximum extrusion temperature must be at least 10° C. below the melting point.

It follows from the discussion above that for a carrier system to be viable with a particular form of fine drug particles it must be hot-melt extrudable at temperatures below the maximum extrusion temperature of the active. If the carrier system does not become molten at the highest processing temperatures, an acceptable extruded product will not be formed. Therefore, the most appropriate extrusion temperature is that which makes the carrier system molten and is below the solubilization and/or recrystallization temperature of the active particles.

Other process variables such as feed rate and screw speed are optimized to provide adequate shear and mixing so that the fine drug particles are deaggregated and well dispersed as primary particles in the matrix of the carrier. The effect of feed rate and screw speed on such dependent variables as the level of shear and mixing inside the extruder depends heavily on the design of the equipment and namely the screw elements. Generally, increasing the screw speed will increase the shear forces between the screw element and the barrel wall, thereby allowing for more rigorous mixing and a greater extent of particle deaggregation. Decreasing the feed rate (non-flood feeding) will generally allow for more complete mixing and particle deaggregation due a reduction in the amount of material within the extruder. For the present invention, there should be sufficient shearing to deaggregate the fine drug particles and homogenously disperse the resulting primary particles throughout the carrier matrix. To determine adequate shearing, the extruded product can be examined by SEM to observe a typical particle size and degree of particle separation. If unsatisfactory deaggregation or dispersion is seen, the feed rate may be reduced and/or screw speed increased to increase the vigor of the mixing. It may also be beneficial to reprocess the material by hot-melt extrusion one or more times to achieve a homogenous deaggregated dispersion.

Consideration should be given to the manner in which the components of a formulation are fed to the extruder. In some embodiment, all formulation components are blended together to form a blended mixture before being fed to the extruder. This can be done by any traditional mixing or blending technique. Alternatively, formulation components may be fed individually if done simultaneously, and given that there is adequate mixing of the formulation components in the mixing/conveying zone of the extruder.

A desiccant can be used to aid in storing a formulation according to the invention in order to help maintain a stable release profile. Suitable desiccants include sodium sulfate, calcium sulfate, magnesium sulfate, sodium hydroxide, sodium bicarbonate, clay, vermiculite, paper, activated alumina, zeolite, calcium chloride, molecular sieve, or anhydrous chemicals. Accordingly, the method of invention for stabilizing the release profile of a film-coated dosage form can comprise the step of including a desiccant in the container in which the dosage form is stored. In some cases a desiccant is needed if the carrier materials of the drug are hygroscopic since moisture may affect the physical stability of the primary crystalline or amorphous particles.

Figure 8:
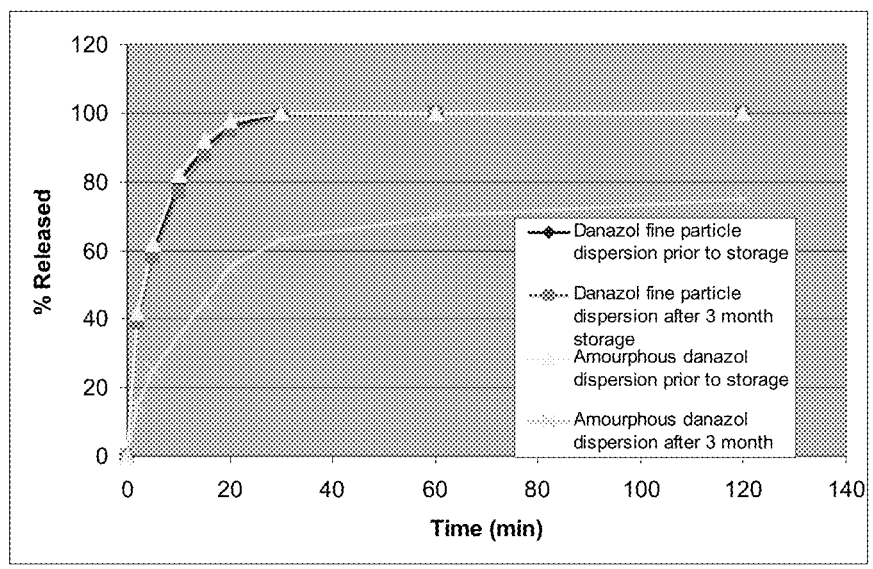

The influence of storage time, temperature and relative humidity upon the release profiles of composition made herein is depicted in FIG. 8. FIG. 8 compares, before and after storage, the release profiles of danazol dispersions made according to the proposed invention with an amorphous solid solution of danazol whereby amorphous drug particles are formed in-situ during hot-melt extrusion. Lines on FIG. 8 denoted by triangular and diamond shaped markers represent the two formulations prior to storage, both showing similar release profiles. Lines on FIG. 8 denoted by square and x shaped markers show the dissolution profile of the two formulations after three month storage in sealed containers at 40° C. and 75%. It can be seen that the dissolution rate of the danazol dispersion produced by in-situ formation of amorphous danazol particles is significantly decreased after storage. This is the result of agglomeration and recrystallization of amorphous danazol particles due to the perturbations during storage. This decrease is not seen in the case of the formulation produced according to the proposed invention because fine drug particles of danazol are stabilized against recrystallization by formulation with a stabilizing excipient during the production of the particles. Additionally aggregation of fine danazol particles is prevented by the stabilizing nature of the carrier system. Thus, the physical stability of the fine drug particles is maintained and hence the dissolution profile is maintained unchanged with storage.

Figure 9:
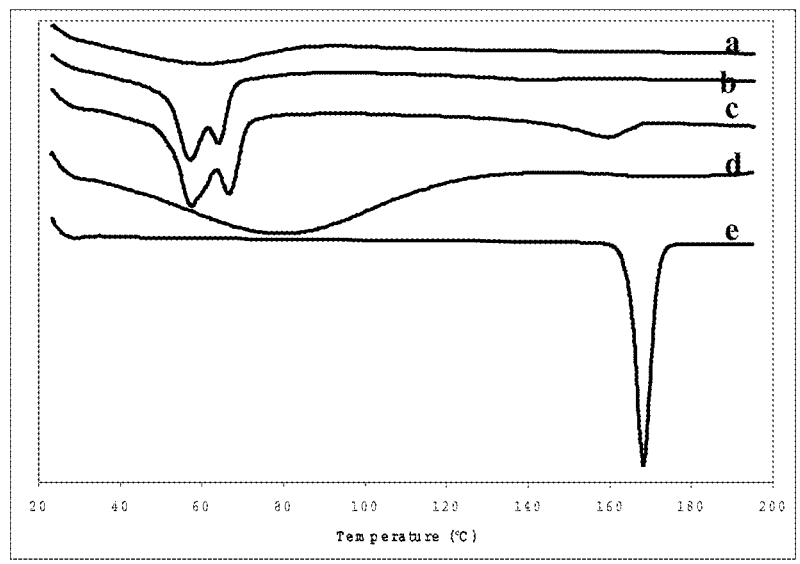
FIG. 9 depicts DSC thermograms obtained according to Example 3 of PVP-stabilized amorphous ITZ particles (Example 9), extrudates containing PVP-stabilized amorphous ITZ (Example 10), a physical mixture of crystalline ITZ with the excipient components of Examples 9 and 10, PVP K25, and bulk crystalline ITZ.

FIG. 9 depicts DSC thermograms obtained according to Example 3 of PVP-stabilized amorphous ITZ particles (Example 9), extrudates containing PVP-stabilized amorphous ITZ (Example 10), a physical mixture of crystalline ITZ with the excipient components of Examples 9 and 10, PVP K25, and bulk crystalline ITZ. The DSC thermograms indicate that the PVP-stabilized ITZ particles are substantially amorphous compared to bulk ITZ as seen by the complete absence of an endothermic event at 165° C. that is associated with the melting of crystalline ITZ. The thermograms also demonstrate that the amorphous nature of the PVP-stabilized ITZ particles is maintained during the melt extrusion process as seen by the absence of an endothermic event at approximately 160° C. as is seen with the physical mixture containing crystalline ITZ. This figure demonstrates that the amorphous nature of the PVP-stabilized amorphous ITZ particles is not altered by hot hot-melt extrusion with a non-solubilizing carrier system when extrusion temperatures are well below the $T_g$ (glass transition temperature) the particle composite.

Figure 10:
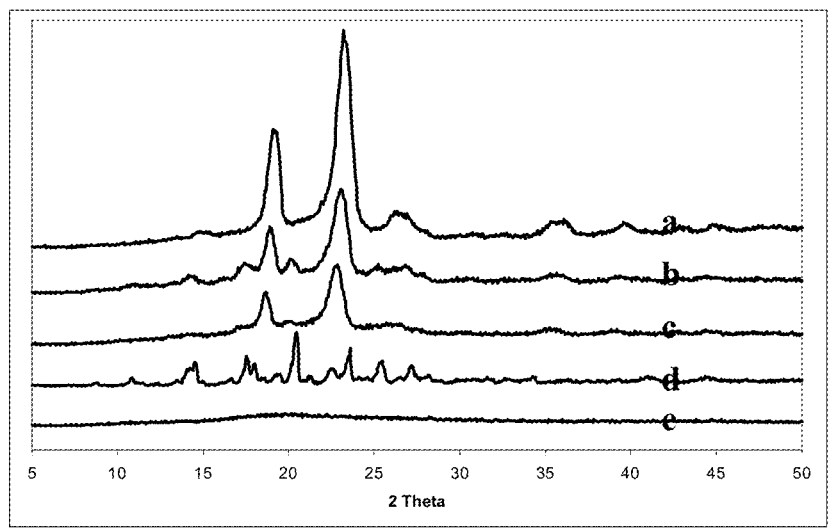
FIG. 10 depicts X-ray diffraction patterns obtained according to Example 11 for poloxamer 407:PEO (7:3) placebo extrudate, a physical mixture of crystalline ITZ with the excipient components of examples 9 and 10, extrudates containing PVP-stabilized amorphous ITZ (Example 10), bulk ITZ, and PVP-stabilized amorphous ITZ (Example 9).

FIG. 10 depicts x-ray diffraction patterns obtained according to Example 11 for poloxamer 407:PEO (7:3) placebo extrudate, a physical mixture of crystalline ITZ with the excipient components of Examples 9 and 10, extrudates containing PVP-stabilized amorphous ITZ (Example 10), bulk ITZ, and PVP-stabilized amorphous ITZ (Example 9). The results show a substantially amorphous content of drug for both Example 9 and Example 10 when compared to the control bulk crystalline itraconazole sample and physical mixture. The peaks noted with the red arrows are peaks associated with crystalline ITZ as are seen with the bulk drug and the physical mixture, yet not seen in Example 9 or 10. This figure serves as supplemental analysis to DSC in its demonstration that the amorphous nature of the PVP-stabilized amorphous ITZ particles is not altered by hot-melt extrusion with a non-solubilizing carrier system when extrusion temperatures are sufficiently below the $T_g$ the particle composite.

Figure 11A:
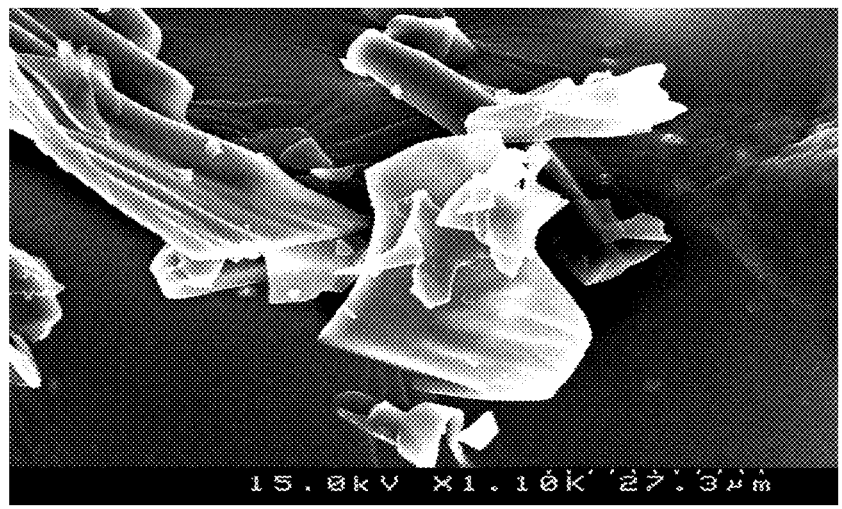
FIGS. 11a-11d depict SEM (scanning electron microscopy) images obtained according to Example 2 for samples prepared according to Example 9 (FIG. 11a), a Poloxamer: PEO (7:3) placebo extrudate (FIG. 11b), and samples prepared according Example 10 (FIGS. 11c and 11d).
Figure 11B:
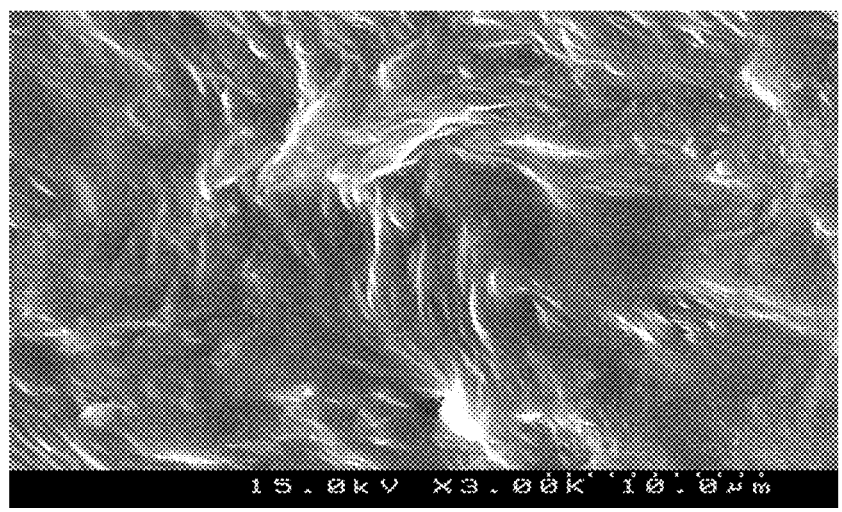
Figure 11C:
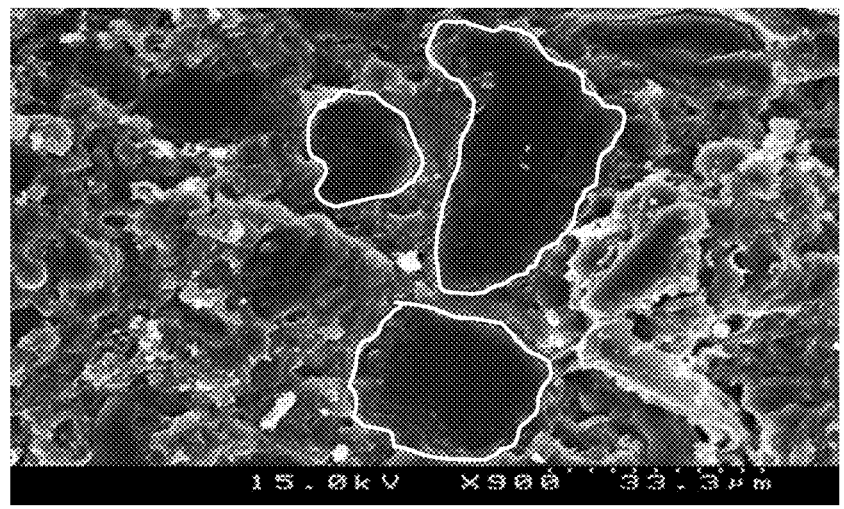
Figure 11D:
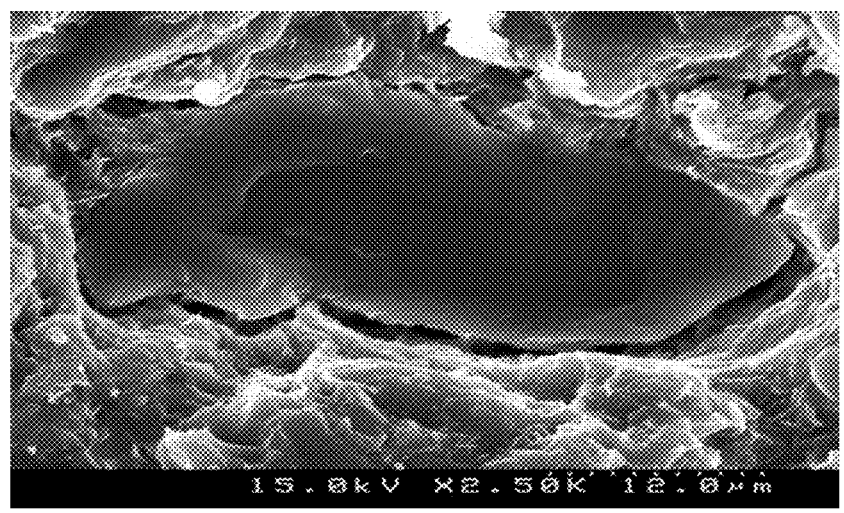

FIGS. 11a-11d depict SEM images obtained according to Example 2 for samples prepared according to Example 9 (FIG. 11a), a Poloxamer:PEO (7:3) placebo extrudate (FIG. 11b), and samples prepared according Example 10 (FIGS. 11c and 11d). From a comparison of the SEM images, it can be seen that the PVP-stabilized amorphous ITZ particles are not molten during hot-melt extrusion and are dispersed within the polymer matrix as discernable, individualized particles by the hot-melt extrusion process.

Figure 12:
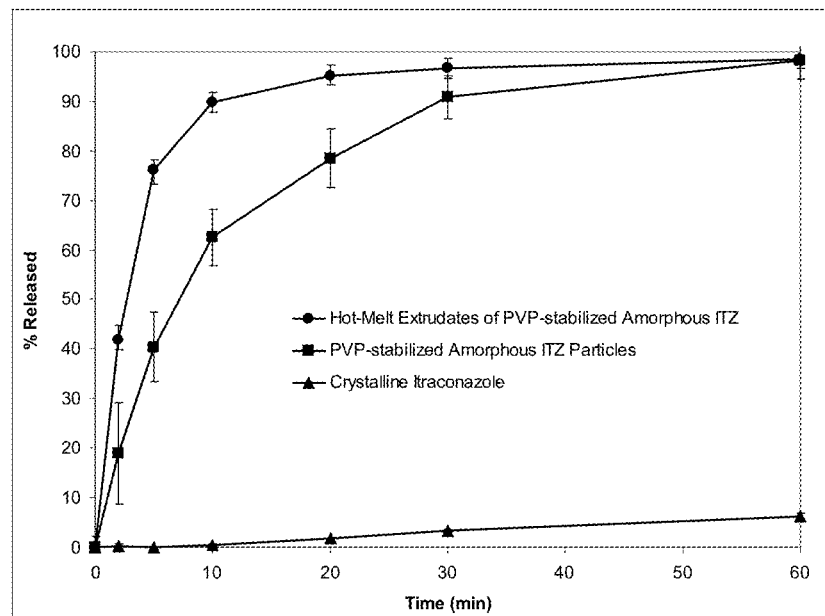
FIG. 12 depicts comparative dissolution test (drug release) profiles obtained according to Example 12 for samples made according to Example 10, samples made according to Example 9, and bulk ITZ.

FIG. 12 depicts the results of a comparative dissolution test obtained according to Example 12 for samples made according to Example 10, samples made according to Example 9, and bulk ITZ. The figure demonstrates that the dissolution rate of ITZ is faster in the case of the extrudates than the amorphous particles alone with 90% drug release in 10 minutes compared to 62%, respectively. Both the extrudates and the amorphous particles exhibited substantially faster dissolution rates over the bulk ITZ as the bulk ITZ showed less than 1% dissolved in 10 minutes. This figure demonstrates that hot-melt extrusion of PVP-stabilized amorphous ITZ particles in a hydrophilic carrier improves the dissolution properties of the particles. This improvement is the result of increased surface area and enhanced wettability of the drug particles by deaggregation and dispersion of the particles into a hydrophilic carrier via the hot-melt extrusion process. The substantial improvement of the extrudates and the amorphous particles alone over the bulk ITZ demonstrates the benefit of formulating ITZ in the amorphous state for achieving rapid dissolution.

Figure 13:
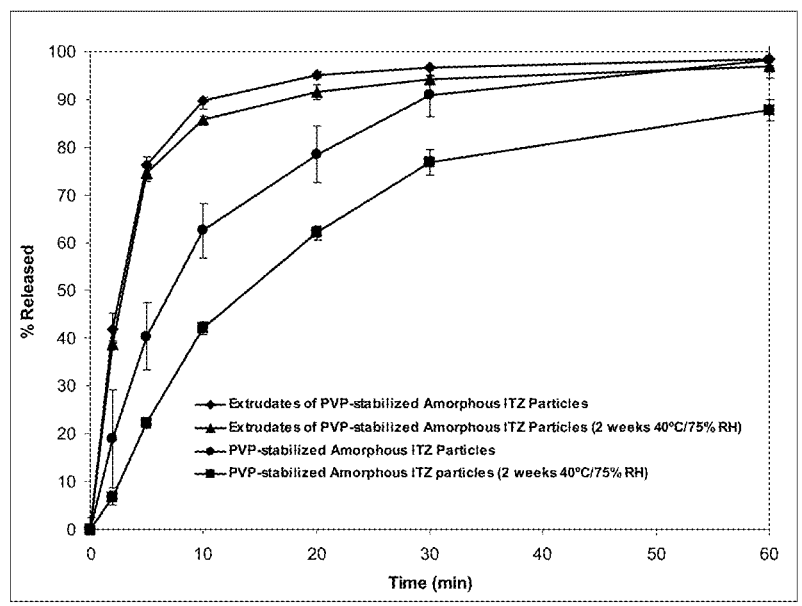
FIG. 13 depicts comparative dissolution profiles obtained according to Example 4 for samples made according to Example 9 and Example 10 before and after storage at conditions of 40° C. and 75% relative humidity in aluminum induction sealed high density polyethylene bottles for a period of two weeks.

FIG. 13 depicts comparative dissolution profiles for samples made according to Example 9 and samples made according to Example 10 before and after storage according to Example 4 at conditions of 40° C. and 75% relative humidity in aluminum induction sealed high density polyethylene bottles for a period of two weeks. The dissolution profile of the hot-melt extruded amorphous ITZ particles is stable on storage for 2 weeks, whereas the dissolution profile of the amorphous particles alone is unstable as it was substantially decreased on storage. This figure demonstrates the effect that hot-melt extruding the amorphous ITZ particles in a stabilizing carrier system has upon dissolution profile stability. The stabilizing carrier system protects the drug particles from ambient moisture absorption that would otherwise lead to particle aggregation and recrystallization of the amorphous drug. The aforementioned effects of ambient moisture absorption are clearly seen with the decrease in dissolution rate of the amorphous ITZ particles after 2 weeks storage.

Figure 14:
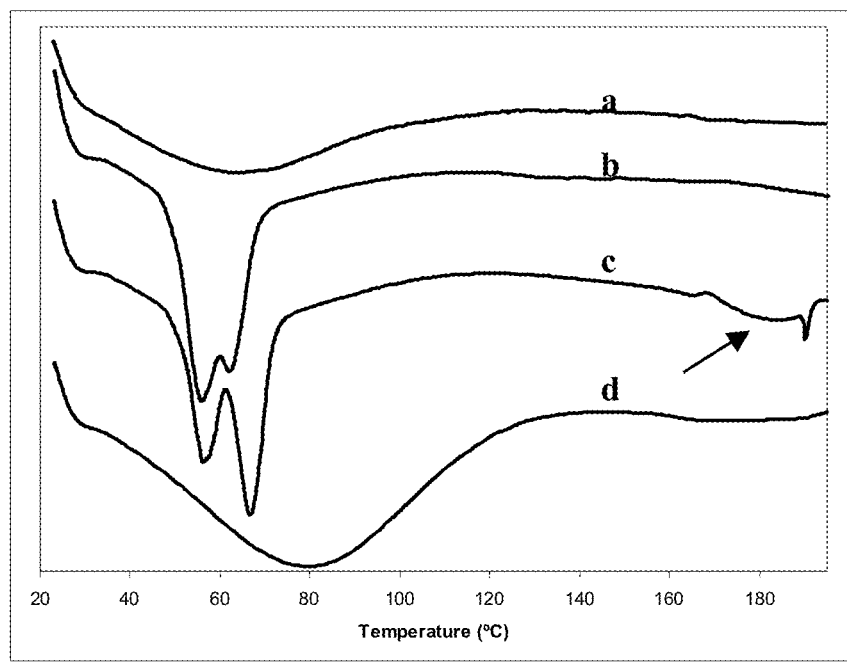
FIG. 14 depicts DSC thermograms obtained according to Example 3 for samples prepared according to Example 13, samples prepared according to Example 14, a physical mixture of crystalline CBM with the excipient components of examples 13 and 14, and PVP K25.

FIG. 14 depicts DSC thermograms obtained according to Example 3 for samples produced according to Example 13, samples produced according to Example 14, a physical mixture of crystalline CBM with the excipient components of examples 13 and 14, and PVP K25. The DSC thermograms indicate that the PVP-stabilized CBM particles are substantially amorphous as seen by the complete absence of the endothermic event at 190° C. that is associated with the melting of crystalline CBM. The thermograms also indicate that the morphology of PVP-stabilized amorphous CBM particles was not altered by the hot-melt extrusion process as seen by the absence of the broad endothermic event in the range of 170 to 190° C. that is associated with the melting of crystalline CBM in the presence of the other excipients as seen with the physical mixture. This figure therefore demonstrates that the morphology of the PVP-stabilized amorphous CBM particles is not altered by hot-melt extrusion with a non-solubilizing carrier formulation when extrusion temperature is sufficiently lower than the $T_g$ of the particle composite.

Figure 15:
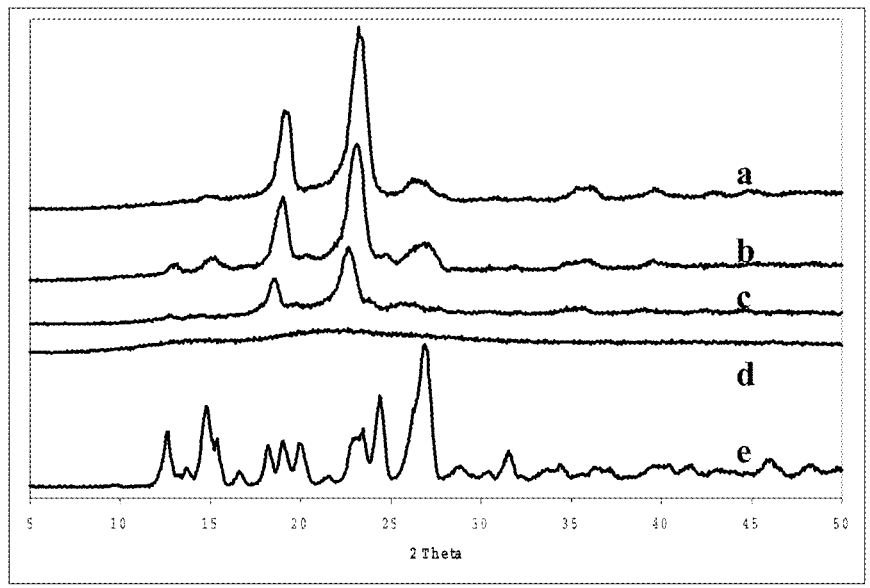
FIG. 15 depicts X-ray diffraction patterns obtained according to Example 11 for poloxamer 407:PEO (7:3) placebo extrudate, a physical mixture of crystalline CBM with the excipient components of Examples 13 and 14, samples produced according to Example 14, samples produced according to Example 13, and bulk CBM.

FIG. 15 depicts x-ray diffraction patterns obtained according to Example 11 for poloxamer 407:PEO (7:3) placebo extrudate, a physical mixture of crystalline CBM with the excipient components of Examples 13 and 14, samples produced according to Example 14, samples produced according to Example 13, and bulk CBM. The data indicate a substantially amorphous content of drug for both Example 13 and Example 14 when compared to the control bulk crystalline itraconazole sample and physical mixture. The peaks noted with the arrows are peaks associated with crystalline CBM as are seen with the bulk drug and the physical mixture, yet not seen with the sample of either Example 13 or Example 14. This figure serves as supplemental analysis to DSC in its demonstration that the amorphous nature of the PVP-stabilized amorphous CBM particles is not altered by hot-melt extrusion with a non-solubilizing carrier system when extrusion temperatures are well below the $T_g$ the particle composite.

Figure 16:
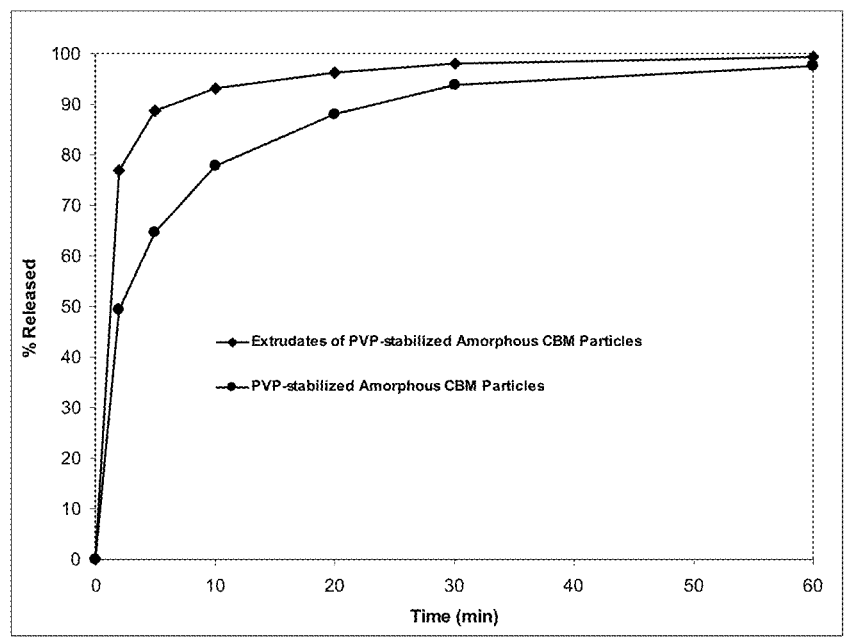
FIG. 16 depicts comparative dissolution profiles obtained according to Example 12 for samples made according to Example 13 and Example 14.

FIG. 16 comparative dissolution profiles obtained according to Example 12 for samples made according to Example 13 and samples made according to Example 14. The figure demonstrates that the dissolution rate of CBM is faster in the case of the extrudates than the amorphous particles alone with 93% drug release in 10 minutes compared to 78%, respectively. This figure demonstrates that hot-melt extruding PVP-stabilized amorphous CBM particles in a hydrophilic carrier improves the dissolution properties of the particles. This improvement is the result of increased surface area and enhanced wettability of the drug particles by deaggregation and dispersion of the particles into a hydrophilic carrier via the hot-melt extrusion process.

Figure 17:
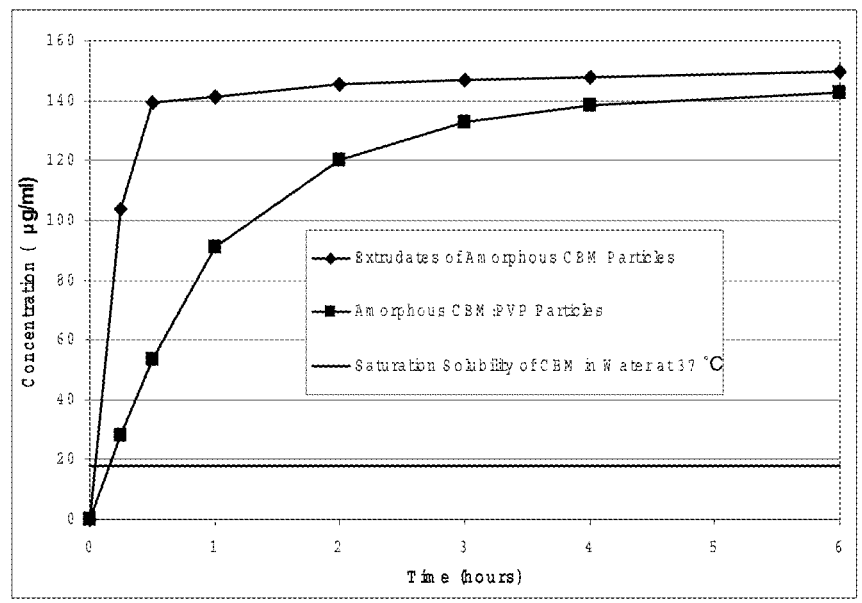
FIG. 17 depicts comparative dissolution profiles for samples made according to Example 13 and Example 14 in which the amount of CBM added to each dissolution vessel (200 mg/900 ml) was several times greater than the equilibrium saturation solubility.

FIG. 17 depicts comparative dissolution profiles for samples made according to Example 13 and Example 14 in which the amount of CBM added to each dissolution vessel (200 mg/900 ml) was several times greater than the equilibrium saturation solubility. This is in contrast to the previous figure where the concentration of the drug in each dissolution vessel (10 mg/900 ml) was below the equilibrium solubility. This figure demonstrates that extrudates containing CBM amorphous particles reach higher levels of supersaturation with a much more rapid dissolution rate than the amorphous particles alone. Because of the increased amount of material in each dissolution vessel, the hydrophobic attraction of the amorphous CBM particles in the dissolution media that causes them to aggregate and which impedes dissolution was more pronounced. This hydrophobic attraction is greatly reduced by hot-melt extruding the CBM amorphous particles in a hydrophilic carrier which renders the particles more wettable, and thus increases the rate and extent of dissolution.

Figure 18:
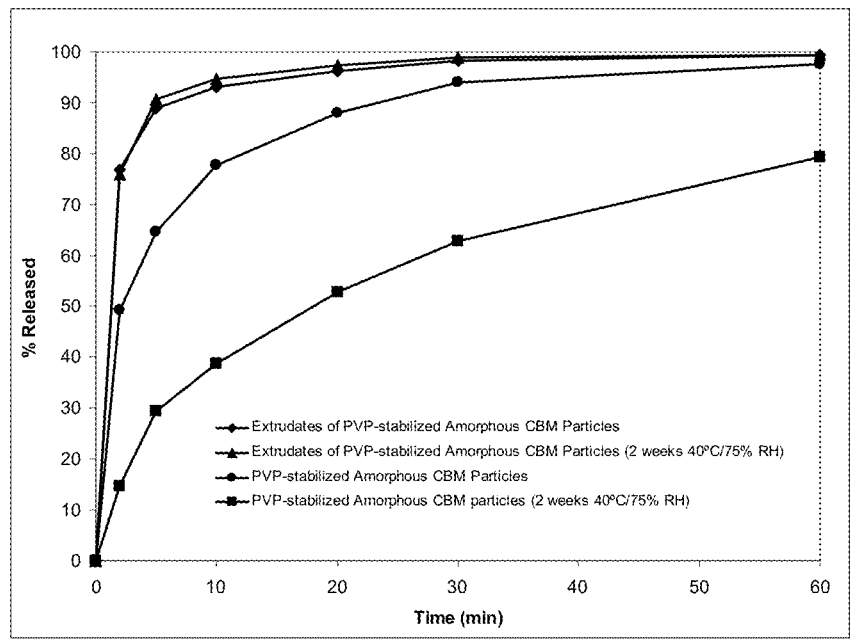
FIG. 18 depicts comparative dissolution profiles for samples made according to Example 13 and samples made according to Example 14 before and after storage according to Example 4 at conditions of 40° C. and 75% relative humidity in aluminum induction sealed high density polyethylene bottles for a period of two weeks.

FIG. 18 depicts comparative dissolution profiles for samples made according to Example 13 and samples made according to Example 14 before and after storage according to Example 4 at conditions of 40° C. and 75% relative humidity in aluminum induction sealed high density polyethylene bottles for a period of two weeks. It can be seen in the figure that the dissolution profile of the hot-melt extruded amorphous CBM particles is stable following 2 weeks of storage, whereas the dissolution profile of the amorphous particles alone is unstable as it was substantially decreased on storage. This figure demonstrates the effect of hot-melt extruding the amorphous CBM particles in a stabilizing carrier system that protects them from ambient moisture absorption that leads to particle aggregation and recrystallization of the amorphous drug. The aforementioned effects of ambient moisture absorption are clearly seen by the decrease in dissolution rate of the amorphous CBM particles after 2 weeks storage.

Figure 19:
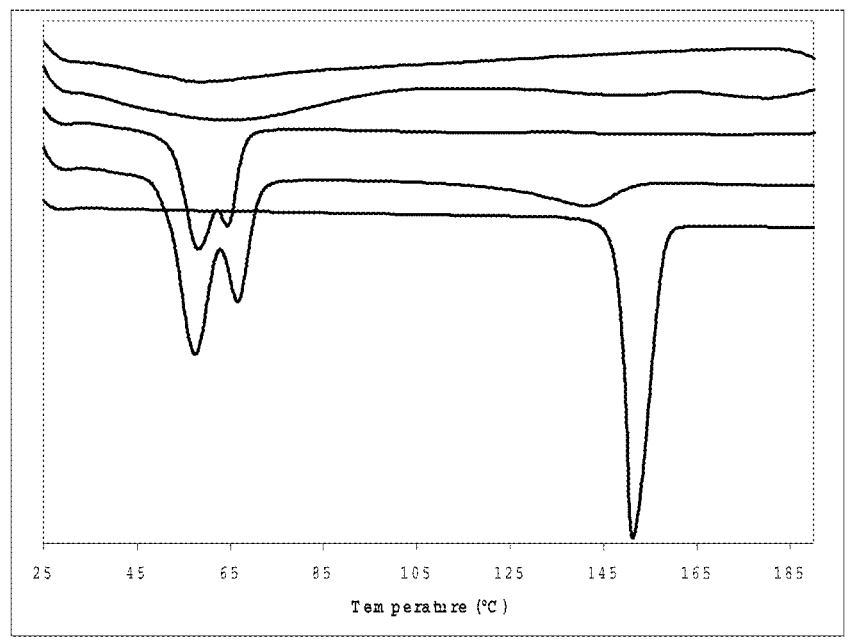
FIG. 19 depicts DSC thermograms obtained according to Example 3 for samples produced according to Example 15, HPMC E3, samples produced according to Example 16, a physical mixture of crystalline KCZ with the excipient components of Examples 15 and 16, and bulk ketoconazole.

FIG. 19 depicts DSC thermograms obtained according to Example 3 for samples produced according to Example 15, HPMC E3, samples produced according to Example 16, a physical mixture of crystalline KCZ with the excipient components of Examples 15 and 16, and bulk ketoconazole. The DSC thermograms indicate that the HPMC-stabilized KCZ particles are substantially amorphous compared to bulk ketoconazole as seen by the complete absence of the endothermic event at 151° C. associated with the melting of crystalline KCZ. The thermograms also indicate that the morphology of HPMC-stabilized amorphous KCZ particles was not altered by the hot-melt extrusion process. This is evidenced by the absence of the broad endothermic event with the peak value at 142° C. observed with the physical mixture, which peak is associated with the melting of crystalline KCZ in the presence of the other excipients. This figure therefore demonstrates that the morphology of the HPMC-stabilized amorphous KCZ particles is not altered by hot-melt extrusion with a non-solubilizing carrier formulation when extrusion temperature is sufficiently lower than the $T_g$ of the particle composite.

Figure 20A:
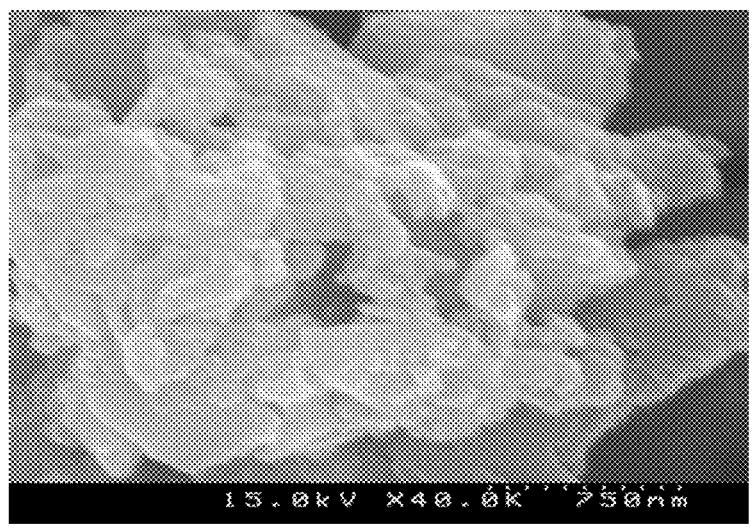
FIG. 20a-20b depict SEM images obtained according to Example 2 for samples prepared according to Example 17 (FIG. 20a) and Example 18 (FIG. 20b). The circles in FIG. 20b highlight some of the more apparent fine crystals of Danazol that are dispersed in the polymeric carrier matrix.
Figure 20B:
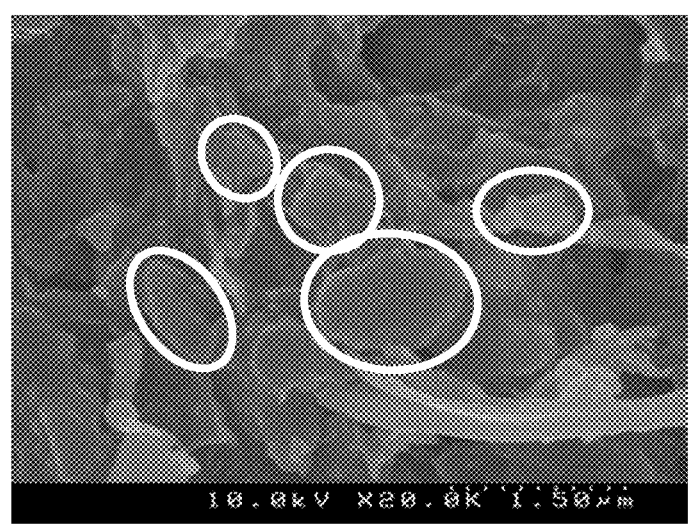

FIGS. 20a-20b depict SEM images obtained according to Example 2 of samples prepared according to Example 17 (FIG. 20a) and samples prepared according Example 18 (FIG. 20b). FIG. 20a depicts a large aggregate of fine crystalline DNZ particles, with some of the smaller particles having diameters near 100 nm. FIG. 20b depicts fine crystalline DNZ particles hot-melt extruded with a non-solubilizing polymeric carrier. It can be seen from the figure that large aggregates of fine crystalline DNZ particles are broken up and dispersed within the polymeric matrix as discernable, individualized particles by the hot-melt extrusion process. Additionally, it can be seen that the individual DNZ particles are not solubilized by the polymeric carrier during hot-melt extrusion.

In view of the present disclosure, the invention provides a pharmaceutical composition possessing a stabilized release profile, the composition comprising fine drug-containing particles dispersed in a nonsolubilizing and stabilizing carrier, the pharmaceutical composition having been prepared by a method comprising the step of: providing a charge of fine drug-containing particles of a therapeutic compound;

providing a charge of stabilizing and non-solubilizing hot-melt extrudable carrier; and mixing and hot-melting extruding the charges to form the hot-melt extruded pharmaceutical composition; wherein a substantial majority of the fine drug particles are not agglomerated or aggregated during the step of hot-melt extruding.

As used herein, the term "opaquant" is intended to mean a compound used to render a composition opaque. May be used alone or in combination with a colorant. Such compounds include, by way of example and without limitation, titanium dioxide and other materials known to one of ordinary skill in the art.

Some of the materials listed herein may be too brittle or may have Tg values that are generally too high rendering them too difficult to extrude. The glass transition temperature is reduced upon the addition of a plasticizer. As used herein, the glass transition temperature is taken to mean the temperature at which a solid material softens or melts (or the glass transition temperature (Tg) is the temperature at which a polymer changes during the heat cycle from a brittle substance (glass) to a rubbery mass). Such materials can be combined with one or more plasticizers to render them thermoformable. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the film of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly(ethylene glycol) *Chemistry: Biotechnical and Biomedical Applications* (J. M. Harris, Ed.; Plenum Press, NY) the disclosure of which is hereby incorporated by reference.

Preservatives include compounds used to prevent the growth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The solid substrate of the invention will include an active agent when included in a dosage form. Generally an effective amount of active agent is included. By the term "effective amount", it is understood that, with respect to, for example, pharmaceuticals, a therapeutically effective amount is contemplated. A therapeutically effective amount is the amount or quantity of drug that is sufficient to elicit the required or desired therapeutic response, or in other words, the amount that is sufficient to elicit an appreciable biological response when administered to a patient.

The active agent can be present in its free acid, free base or pharmaceutically acceptable salt form. As used herein, "pharmaceutically acceptable salts" refer to derivatives of the disclosed compounds wherein the active agent is modified by making acid or base salts thereof. Examples of pharmaceutically acceptable salts include, but are not limited to, mineral or organic acid salts of the drug. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and other known to those of ordinary skill in the pharmaceutical sciences. Lists of suitable salts are found in texts such as *Remington's Pharmaceutical Sciences*, 18th Ed. (Alfonso R. Gennaro, ed.; Mack Publishing Company, Easton, Pa., 1990); *Remington: the Science and Practice of Pharmacy* 19$^{th}$ Ed. (Lippincott, Williams & Wilkins, 1995); *Handbook of Pharmaceutical Excipients*, 3rd Ed. (Arthur H. Kibbe, ed.; Amer. Pharmaceutical Assoc., 1999); the *Pharmaceutical Codex: Principles and Practice of Pharmaceutics* 12$^{th}$ Ed. (Walter Lund ed.; Pharmaceutical Press, London, 1994); The United States Pharmacopeia: The National Formulary (United States Pharmacopeial Convention); and *Goodman and Gilman's: the Pharmacological Basis of Therapeutics* (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "therapeutic compound", "therapeutic agent", "active agent" and "drug" are used interchangeably, unless otherwise specified. The process of the invention can be used to prepare composition and dosage forms comprising essentially any one or more active agents. Active agents include physiological substances or pharmacological active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, minerals, dietary supplements, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleansing, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

Further therapeutic compounds which can be formulated into the present composition also include antibacterial substance, antihistamine (histamine receptor inhibitor), decongestant, anti-inflammatory agent, antiparasitic agent, antiviral agent, local anesthetic, antifungal agent, amoebicidal agent, trichomonocidal agent, analgesic agent, antiarthritic agent, antiasthmatic agent, anticoagulant agent, anticonvulsant agent, antidepressant agent, antidiabetic agent, antineoplastic agent, antipsychotic agent, neuroleptic agent, antihypertensive agent, muscle relaxant, depressant agent, hypnotic agent, sedative agent, psychic energizer, tranquilizer, antiparkinson agent, muscle contractant, anti-microbial agent, antimalarial agent, hormonal agent, contraceptive agent, sympathomimetic agent, diuretic agent, hypoglycemic agent, ophthalmic agent, anti-hypercholesterolemia agent, anti-hypocholesterolemia agent, electrolyte, diagnostic agent, cardiovascular drug, vitamin, nutrient, other type of therapeutic compound known to those of ordinary skill in the pharmaceutical sciences, and combinations thereof.

Representative active agents include nutrients and nutritional agents, hematological agents, endocrine and metabolic agents, cardiovascular agents, renal and genitourinary agents, respiratory agents, central nervous system agents, gastrointestinal agents, anti-infective agents, biologic and immunological agents, dermatological agents, ophthalmic agents, antineoplastic agents, and diagnostic agents. Exemplary nutrients and nutritional agents include as minerals, trace elements, amino acids, lipotropic agents, enzymes and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes.

Exemplary cardiovascular agents include nootropic agents, antiarrhythmic agents, calcium channel blocking agents, vasodilators, antiadrenergics/sympatholytics, renin angiotensin system antagonists, antihypertensive combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, nasal decongestants, respiratory enzymes, lung surfactants, antihistamines, nonnarcotic antitussives, and expectorants. Exemplary central nervous system agents include CNS stimulants, narcotic agonist analgesics, narcotic agonist-antagonist analgesics, central analgesics, acetaminophen, salicylates, nonnarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including H pylori agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, esomeprazole, famotidine, lansoprazole, omeprazole, pantoprazole, rabeprazole, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, such as amoxicilin, cephalosporins and related antibiotics, carbapenem, monobactams, chloramphenicol, quinolones, fluoroquinolones, tetracyclines, macrolides, such as azithromycin, clarithromycin, and the like, spectinomycin, streptogramins, vancomycin, oxalodinones, lincosamides, oral and parenteral aminoglycosides, colistimethate sodium, polymyxin B sulfate, bacitracin, metronidazole, sulfonamides, nitrofurans, methenamines, folate antagonists, antifungal agents, such as fluconazole, voriconazole, and the like, antimalarial preparations, antituberculosis agents, amebicides, antiviral agents, antiretroviral agents, leprostatics, antiprotozoals, anthelmintics, and CDC anti-infective agents. Exemplary biologic and immunological agents including immune globulins, monoclonal antibody agents, antivenins, agents for active immunization, allergenic extracts, immunologic agents, and antirheumatic agents. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, DNA topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

Representative antibacterial substances are beta-lactam antibiotics, tetracyclines, chloramphenicol, neomycin, gramicidin, bacitracin, sulfonamides, aminoglycoside antibiotics, tobramycin, nitrofurazone, nalidixic acid, penicillin, tetracycline, oxytetracycline, chlorotetracycline, erythromycin, cephalosporins and analogs and the antimicrobial combination of fludalanine/pentizidone. Other representative antibacterial agents include of the poorly water-soluble pyrridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof.

Representative antiparasitic compounds are ivermectin, bephenium, hydroxynaphthoate, praziquantel, nifurtimox, benznidasol, dichlorophen and dapsone. Representative anti-malarial compounds are 4-aminoquinolines, 8-aminoquinolines and pyrimethamine.

Representative antiviral compounds are protease inhibitors, neuramidinase inhibitors, commercially available compounds, acyclovir and interferon.

Representative anti-inflammatory drugs include specific or selective COX-2 receptor inhibitors, rofecoxib, celecoxib, etodolac, flurbiprofen, ibuprofen, ketoprofen, ketorolac, nabumetone, piroxicam, suprofen, tolmetin, zileuton, steroids, cyclooxygenase inhibitors, cortisone, hydrocortisone, betamethasone, dexamethasone, fluocortolone, prednisolone, phenylbutazone, triamcinolone, sulindac, indomethacin, salicylamide, naproxen, colchicine, fenoprofen, diclofenac, indoprofen, dexamethasone, allopurinol, oxyphenbutazone, probenecid and sodium salicylamide.

Representative analgesic drugs are diflunisal, aspirin, ibuprofen, profen-type compounds, morphine, codeine, levorphanol, hydromorphone, oxymorphone, oxycodone, hydrocodone, naloxene, levallorphan, etorphine, fentanyl, bremazocine, meperidine, nalorphine, tramadol, and acetaminophen.

Representative antihistamines and decongestants are acrivastine, astemizole, norastemizol, brompheniramine, cetirizine, clemastine, diphenhydramine, ebastine, famotidine, fexofenadine, meclizine, nizatidine, perilamine, promethazine, ranitidine, terfenadine, chlorpheniramine, cimetidine, tetrahydrozoline, tripolidine, loratadine, desloratadine, antazoline, and pseudoephedrine.

Representative antiasthma drugs are theophylline, ephedrine, beclomethasone dipropionate and epinephrine.

Representative anticoagulants are heparin, bishydroxycoumarin, and warfarin.

Representative psychic energizers are isocoboxazid, nialamide, phenelzine, imipramine, tranycypromine, and parglyene.

Representative anticonvulsants are clonazepam, phenobarbital, mephobarbital, primidone, enitabas, diphenylhydantion, ethltion, pheneturide, ethosuximide, diazepam, phenytoin carbamazepine, lamotrigine, lorazepam, levetiracetam, oxcarbazepine, topiramate, valproic acid, chlorazepate, gabapentin, felbamate, tiagabine and zonisamide.

Representative antidepressants are amitriptyline, chlordiazepoxide perphenazine, protriptyline, imipramine, doxepin, venlafaxine, o-desmethyl venlafaxine, citalopram, escitalopram, bupropion, clomipramine, desipramine, nefazodone, fluoxetine, fluvoxamine, maprotiline, mirtazapine, nortriptyline, paroxetine, phenelzine, tranylcypromine, sertraline, trazodone, trimipramine, and amoxapine.

Representative antidiabetics are sulphonylureas, such as tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones (glitazones), such as rosiglitazone, pioglitazone, and troglitazone; biguanidines, such as metformin; and other antidiabetic agents, such as nateglinide, repaglinide, insulin, somatostatin and its analogs, chlorpropamide, isophane insulin, protamine zinc insulin suspension, globin zinc insulin, and extended insulin zinc suspension.

Representative antineoplastics are chlorambucil, cyclophosphamide, triethylenemelamine, thiotepa, hexamethylmelamine, busulfan, carmustine, lomustine, dacarbazine, arabinoside cytosine, mercaptopurine, azathiprine, vincristine, vinblastine, taxol, etoposide, actinomycin D, daunorubicin, doxorubicin, bleomycin, mitomycin; cisplatin; hydroxyurea, procarbazine, aminoglutethimide, tamoxifen, adriamycin, fluorouracil, methotrexate, mechlorethamine, uracil mustard, 5-fluorouracil, 6-6-thioguanine and procarbazine asparaginase.

Representative steroidal drugs are prednisone, prednisolone, cortisone, cortisol and triamcinolone; androgenic steroids such as methyltesterone, and fluoxmesterone; estrogenic steroids such as 17β-estradiol, α-estradiol, estriol, α-estradiol 3 benzoate, and 17-ethynylestradiol-3-methyl ether; progestational steriods such as progesterone, 19-norpregn-4-ene-3,20-dione, 17-hydroxy-19-nor-17-α-pregn-5 (10)-ene-20-yn-3-one, 17α-ethynyl-17-hydroxy-5 (10)-estren-3-one, and 9β, 10α-pregna-4,6-diene-3,20-dione.

Representative estrogen antagonist-agonist drugs are clomiphene citrate and raloxifene HCl.

Representative antipsychotics are prochlorperazine, lithium carbonate, lithium citrate, thioridazine, molindone, fluphenazine, trifluoperazine, perphenazine, amitriptyline, trifluopromazine, chlorpromazine, clozapine, haloperidol, loxapine, mesoridazine, olanzapine, quetiapine, ziprasidone, risperidone, pimozide, mesoridazine besylate, chlorprothixene, and thiothixene.

Representative hypnotics and sedatives are pentobarbital sodium, phenobarbital, secobarbital, thiopental, heterocyclic hypnotics, dioxopiperidines, imidazopyridines, such as zolpidem tartrate, glutarimides, diethylisovaleramide, α-bromoisovaleryl urea, urethanes, disulfanes.

Representative antihypertensives are nifedipine, verapamil, diltiazem, felodipine, amlodipine, isradipine, nicardipine, nisoldipine, nimodipine, bepridil, enalapril, captopril, lisinopril, benazepril, enalaprilat, espirapril, fosinopril, moexipril, quinapril, ramipril, perindopril, trandolapril, furosemide, bumetanide, ethacrynic acid, torsemide, muzolimide, azosemide, piretanide, tripamide, hydrochlorothiazide, chlorthalidone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide, benzothiazide, spironolactone, methyldopa, hydralazine, clonidine, chlorothiazide, deserpidine, timolol, propranolol, metoprolol, pindolol, acebutolol, prazosin hydrochloride, methyl dopa (L-β-3,4-dihydroxyphenylalanine), pivaloyloxyethyl ester of α-methyldopa hydrochloride dihydrate, candesartan cilexetil, eprosartan mesylate, losartan potassium, olmersartan medoxomil, telmisartan, valsartan, and reserpine.

Representative tranquilizers are chloropromazine, promazine, fluphenazine, reserpine, deserpidine, meprobamate, and benezodiazepines (anxyiolitic, sedatives, and hypnotics) such as alprazolam, chlordiazepoxide, diazepam, lorazepam, oxazepam, temazepam, and triazolam.

Representative anti-spasmodics and muscle contractants are atropine, scopolamine, methscopolamine, oxyphenonium, papaverine, and prostaglandins such as PGE1 PGE2 $PGF_{1\alpha}$ $PGF_{2\alpha}$ and PGA.

Representative local anesthetics are benzocaine, procaine, lidocaine, maepaine, piperocaine, tetracaine and dibucaine.

Representative muscle relaxants are alcuronium, alosetron, aminophylline, baclofen, carisoprodol, chlorphenesin, chlorphenesin carbamate, chlorzoxazone, chlormezanone, dantrolene, decamethonium, dyphylline, eperisione, ethaverine, gallamine triethiodide, hexafluorenium, metaxalone, metocurine iodide, orphenadrine, pancuronium, papaverine, pipecuronium, theophylline, tizanidine, tolperisone, tubocurarine, vecuronium, idrocilamide, ligustilide, cnidilide, senkyunolide, succinylcholine-chloride, danbrolene, cyclobenzaprine, methocarbamol, diazepam, mephenesin, methocarbomal, trihexylphenidyl, pridinol (pridinolum), and biperiden.

Representative anti-Parkinson agents are carbidopa, levodopa, ropinirole, pergolide mesylate, rasagiline, pramipexole, entacapone, benzacide, bromocriptine, selegiline, amantadine, trihexylphenidyl, biperiden, pridinol mesylate, and tolcapone.

Representative anti-Dementia and anti-Alzheimer disease agents are memantine, donepexil, galantamine, rivastigmine, and tacrine Representative sympathomimetic drugs are albuterol, epinephrine, amphetamine ephedrine and norepinephrine.

Representative cardiovascular drugs are procainamide, procainamide hydrochloride, amyl nitrite, nitroglycerin, dipyredamole, sodium nitrate and mannitol nitrate.

Representative diuretics are chlorothiazide, acetazolamide, methazolamide, triamterene, furosemide, indapamide, and flumethiazide.

Representative n-blockers are caravedilol, pindolol, propranolol, practolol, metoprolol, esmolol, oxprenolol, timolol, atenolol, alprenolol, and acebutolol.

Representative phosphodiesterase inhibitors are vardenafil HCl and sildenafil citrate.

Representative antilipemic agents are atorvastatin, cerivastatin, clofibrate, fluvastatin, gemfibrozil, lovastatin, mevinolinic acid, niacin, pravastatin, and simvastatin.

Representative antigout drugs are colchicine, allopurinol, probenecid, sulfinpyrazone, and benzbromadone.

Representative nutritional agents are ascorbic acid, niacin, nicotinamide, folic acid, choline biotin, panthothenic acid, and vitamin $B_{12}$, essential amino acids; essential fats.

Representative electrolytes are calcium gluconate, calcium lactate, potassium chloride, potassium sulfate, sodium chloride, potassium fluoride, ferrous lactate, ferrous gluconate, ferrous sulfate, ferrous fumurate and sodium lactate.

Representative drugs that act on α-adrenergic receptors are clonidine hydrochloride, prazosin, tamsulosin, terazosin, and doxazosin.

Representative mild CNS stimulants are caffeine, modafinil, and methylphenidate hydrochloride.

The formulation of the invention can also be used with unclassified therapeutic agents such as clopidrogel, which is indicated for the reduction of atherosclerotic events (myocardial infarction, stroke, and vascular death) in patients with atherosclerosis documented by recent stroke, recent myocardial infarction, or established peripheral arterial disease.

The active agents (drugs) listed herein should not be considered exhaustive and is merely exemplary of the many embodiments considered within the scope of the invention. Many other active agents can be administered with the formulation of the present invention. Suitable drugs are selected from the list of drugs included herein as well as from any other drugs accepted by the U.S.F.D.A. or other similarly recognized authority in Canada (Health Canada), Mexico (Mexico Department of Health), Europe (European Medicines Agency (EMEA)), South America (in particular in Argentina (Administración Nacional de Medicamentos, Alimentos y Tecnología Medica (ANMAT) and Brazil (Ministério da Saúde)), Australia (Department of Health and Ageing), Africa (in particular in South Africa (Department of Health) and Zimbawe (Ministry of Health and Child Welfare),) or Asia (in particular Japan (Ministry of Health, Labour and Welfare), Taiwan (Executive Yuans Department of Health), and China (Ministry of Health People's Republic of China)) as being suitable for administration to humans or animals. Preferred embodiments of the invention include those wherein the active substance is pharmacologically or biologically active or wherein the environment of use is the GI tract of a mammal.

The amount of therapeutic compound incorporated in each dosage form will be at least one or more unit doses and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. The appreciable biological response may occur as a result of administration of single or multiple unit doses of an active substance. A dosage form according to the invention that comprises two or more active agents can include subtherapeutic amounts of one or more of those active agents such that an improved, additive or synergistic clinical benefit is provided by the dosage form. By "subtherapeutic amount" is meant an amount less than that typically recognized as being therapeutic on its own in a subject to which the dosage form is administered. Therefore, a dosage form can comprise a subtherapeutic amount of a first drug and a therapeutic amount of a second drug. Alternatively, a dosage form can comprise a subtherapeutic amount of a first drug and a subtherapeutic amount of a second drug.

The term "unit dose" is used herein to mean a dosage form containing a quantity of the therapeutic compound, said quantity being such that one or more predetermined units may be provided as a single therapeutic administration.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

Example 1

The following process was used to prepare a hot-melt extruded composition according to the invention. The following ingredients in the amounts indicated were used in preparing hot-melt extruded control and sample compositions containing itraconazole (ITZ) as the active agent. The amounts are indicates in parts by weight.

| No. | ITZ | PEO | HPMC | PVA | SLS | Poloxamer 407 |
|---|---|---|---|---|---|---|
| 1 | 0 | 10 | 0 | 0 | 0 | 0 |
| 2 | 1 | 9 | 0 | 0 | 0 | 0 |
| 3 | 0 | 9 | 1 | 0 | 0 | 0 |
| 4 | 1 | 8 | 1 | 0 | 0 | 0 |
| 5 | 0 | 9 | 0 | 1 | 0 | 0 |
| 6 | 1 | 8 | 0 | 1 | 0 | 0 |
| 7 | 0 | 9 | 0 | 0 | 1 | 0 |
| 8 | 1 | 8 | 0 | 0 | 1 | 0 |
| 9 | 0 | 9 | 0 | 0 | 0 | 1 |
| 10 | 1 | 8 | 0 | 0 | 0 | 1 |

A Randcastle Microtruder RCP-0750 hot-melt extruder equipped with a 6 mm round die was operated at 15 RPM, 0.2-0.3 Drive Amps with an Extrusion Temperature of 100° C. to prepare the composition. All powders were blended in a v-shell blender prior to extrusion. Temperature zones were set as follows: zone 1: 90° C., zone 2: 95° C., zone 3: 100° C., die temperature 100° C. The powder blend was placed in a hopper that is located at the head of a vertical screw such that the material is flood fed by gravity. The residence time of the material in the extruder was approximately three minutes. The extrudate was sheared into approximately one foot sections after exiting the die and placed on an aluminum sheets and allowed to cool at ambient conditions.

Following preparation, the compositions can be analyzed by scanning electron microscopy (SEM), differential scanning calorimetry (DSC), visual inspection, dissolution assays and other suitable methods of analysis.

Example 2

The fine drug-containing particles and compositions containing them were analyzed by scanning electron microscopy using a Hitachi S-4500 scanning electron microscope. Samples were coated with Au/Pd and an accelerating voltage of 5 kV was used.

Example 3

Changes in the degree of crystallization of the fine drug-containing particles, either neat or dispersed within a hot-melt extruded composition, were determined and quantified by differential scanning calorimetry. A TA Instruments Model 2920 calorimeter was used to conduct the analyses. The calorimeter was operated using the following parameters:
Nitrogen Purge Flow Rate: 150 ml/min
Sample Pan: Aluminum (Closed)
Sample Weight: 10-15 mg
Heating Rate: 10° C./min
Range: 20-200° C.

The thermograms obtained from the DSC were analyzed using the TA Universal Analysis Software in which peak minimums are determined by linear baseline method with manually selected limits.

Example 4

The hot-melt extruded compositions were exposed to a variety of different storage conditions prior to determining their release profiles. Samples were stored in sealed containers. Depending upon the conditions being evaluated, the closed containers might include a desiccant such as a silica gel mini-pack (Poly Lam Production Corp.). The containers were filled with hot-melt extruded compositions in an open air environment and then sealed without purging the containers prior to sealing. The containers were then stored as desired under a variety of conditions:
Condition A: 25° C. and 60% RH
Condition B: 40° C. and 0% RH
Condition C: 40° C. and 75% RH Example 5

Formulation:
Micronized Cyclosporine (mean particle diameter 2 microns): 15%
Ethylcellulose: 40%
Polyox 200M: 15%
LHPC: 8%
Lactose 16%
Xylitol: 5%
Vitamin E: 1%

A Randcastle Microtruder RCP-0750 hot-melt extruder equipped with a 6 mm round die was operated at 15 RPM, 0.2-0.3 Drive Amps with an Extrusion Temperature of 100° C. to prepare the composition. All powders were blended in a v-shell blender prior to extrusion. Temperature zones were set as follows: zone 1: 90° C., zone 2: 95° C., zone 3: 100° C., die temperature 100° C. The powder blend was placed in a hopper that is located at the head of a vertical screw such that the material is flood fed by gravity. The residence time of the material in the extruder was approximately three minutes. The extrudate was sheared into approximately one foot sections after exiting the die and placed on an aluminum sheets and allowed to cool at ambient conditions.

Example 6

The following procedure is used for the preparation of danazol nanoparticles using "spray freezing into liquid" technology.

Danazol (0.2% w/v) and PVP K15 (0.2% w/v) were dissolved in acetonitrile (500 ml). Aliquots of the solution (75 ml) were loaded into a high-pressure solution cell and atomized beneath the liquid nitrogen surface at 50 ml/min constant flow using a model 100DX ISCO syringe pump (ISCO, Inc., Lincoln, Nebr.) through a 127 μm I.D. polyetherether ketone (PEEK) tubing nozzle. The PEEK tubing acted as an insulating nozzle that prevented freezing within the nozzle orifice. The resultant frozen microparticles were collected and dried by a VirTis Advantage Tray Lyophilizer (VirTis Inc., Gardiner, N.Y.). The resulting product is a fine powder of aggregated nanoparticles of amorphous danazol complexed with PVP-K15 in a one to one ratio.

Example 7

The following procedure is used for the preparation of danazol nanoparticles using "evaporative precipitation into aqueous solution" (EPAS) technology.

Danazol (2% w/v) and PVP K-15 (1% w/v) were dissolved in 200 ml of dichloromethane. This solution was pumped via an HPLC pump at 2 ml/min through a heat exchange coil set at 80° C. After heating, the solution was sprayed through a fine elliptical conical nozzle at 5000 psi constant pressure into a heated water bath (80° C.) containing PVP K-15 (1% w/v) dissolved in 200 ml deionized water. The resultant dispersion was quenched frozen by injecting it into liquid nitrogen and lyophilized as in example 6. The resulting product is a fine powder of aggregated nanoparticles of amorphous danazol complexed with PVP-K15 in a two to one ratio.

Example 8

Hot-Melt Extrusion of Amorphous Fine Drug Particles of Danazol

Because the fine drug particles described in examples 6 and 7 contain PVP-K15 as a major constituent, which has a glass transition temperature of 150° C., the nanoparticle complex will maintain its integrity and thereby its amorphous state if extruded at temperatures of 100° C. or below. The following is an example of a hot melt extrusion formulation and process by which a homogenous extrudate of individualized and stabilized danazol/PVP K-15 nanoparticles can be produced.

Formulation:
Danazol nanoparticles according to examples 6 or 7: 35%
PEO 200M: 50%
HPMC E15: 15%

Process:
A Randcastle Microtruder RCP-0750 hot-melt extruder equipped with a 6 mm round die was operated at 15 RPM, 0.2-0.3 Drive Amps with an Extrusion Temperature of 90° C. to prepare the composition. All powders were blended in a v-shell blender prior to extrusion. Temperature zones were set as follows: zone 1: 80° C., zone 2: 85° C., zone 3: 90° C., die temperature 90° C. The powder blend was placed in a hopper that is located at the head of a vertical screw such that the material is flood fed by gravity. The residence time of the material in the extruder was approximately three minutes. The extrudate was sheared into approximately one-foot sections after exiting the die and placed on an aluminum sheets and allowed to cool at ambient conditions.

Example 9

The following procedure is used for the preparation of PVP-stabilized amorphous itraconazole particles using an evaporative co-precipitation technology.

Formulation:

| Component | Quantity |
| --- | --- |
| Itraconazole (ITZ) | 50% |
| Polyvinylpyrrolidone (PVP; grade K25) | 50% |
| Dichloromethane | 5 mL/g solids |

Solid components listed the table above were dissolved into the organic solvent with the use of an Aquasonic Model 150T ultrasonicator. The solvent was then completely evaporated in a vacuum chamber at a temperature of 40° C. and pressure of 500 mTorr to yield a dry solid product. The solid product was subsequently triturated in a glass mortar and pestle for 2 to 5 minutes to yield PVP-stabilized amorphous itraconazole particles with individual particle diameters ranging from 2 to 100 µm.

Example 10

Hot-Melt Extrusion of Amorphous Fine Drug Particles of Itraconazole

Because the fine drug particles described in Example 9 contain PVP-K25 as a major constituent, which has a glass transition temperature of approximately 150° C., the amorphous microparticle complex will maintain its integrity and thereby its amorphous state if extruded at temperatures of approximately 100° C. or below. The following is an example of a hot-melt extrusion formulation and process by which a homogenous extrudate of individualized and stabilized itraconazole/PVP-K25 amorphous microparticles can be produced.

Formulation:

| Component | Quantity |
| --- | --- |
| Itraconazole/PVP-K25 amorphous microparticles (Example 9) | 50% |
| Poloxamer 407 | 35% |
| Sentry Poloyox WSR N80 (PEO) | 15% |

Process:
A Randcastle Microtruder RCP-0750 hot-melt extruder equipped with a 4 mm round die was operated at 20 RPM, 0.1-0.2 drive amps, and at a melt temperature of 60° C. to prepare the composition. All powders were blended in a v-shell blender prior to extrusion. Temperature zones were set as follows: zone 1: 40° C., zone 2: 60° C., zone 3: 60° C., die temperature 60° C. The powder blend was placed in a hopper that is located at the head of a vertical screw such that the material is flood fed by gravity. The residence time of the material in the extruder was approximately two minutes. The extrudate was sheared into approximately one foot sections after exiting the die and placed on aluminum sheets and allowed to cool at ambient conditions. After cooling, the extrudates were milled with a ceramic mortar and pestle and passed through a 250 µm sieve.

Example 11

Changes in the degree of crystallization of the fine drug-containing particles, either neat or dispersed within a hot-melt extruded composition, were determined by x-ray diffraction. A model 1710 x-ray diffractometer (Philips Electronic Instruments, Inc., Mahwah, N.J.) using a Cu2α monochromated x-ray source was used to conduct the analyses with a 0.05°/2θ step size and a 2 second dwell time. The output data was plotted as peak intensity versus 2θ angle, and the plots were qualitatively analyzed for the presence of peaks indicating crystallinity of the drug substance.

Example 12

The dissolution profiles of the fine-drug containing particles, either neat or dispersed within a hot-melt extruded composition, were determined using a USP 27 Type II paddle apparatus model VK7000 (Varian Inc., Palo Alto, Calif.) at 37° C. and 50 rpm paddle speed.

The dissolution media was 900 ml of 0.1 N HCl, and was de-aerated with helium for approximately 15 minutes before each dissolution test. In all cases where not otherwise specified, the equivalent to 10 mg of the active ingredient was added to each dissolution vessel.

Example 13

The following procedure is used for the preparation of PVP-stabilized amorphous carbamazepine particles using an evaporative co-precipitation technology.

Formulation:

| Component | Quantity |
| --- | --- |
| Carbamazepine (CBM) | 50% |
| Polyvinylpyrrolidone (PVP; grade K30) | 50% |
| Dichloromethane | 5 mL/g solids |

Procedure:

Solid components listed the table above were dissolved into the organic solvent with the use of an Aquasonic Model 150T ultrasonicator. The solvent was then completely evaporated in a vacuum chamber at a temperature of 40° C. and pressure of 500 mTorr to yield a dry solid product. The solid product was subsequently triturated in a glass mortar and pestle for 2 to 5 minutes to yield PVP-stabilized amorphous carbamazepine particles with individual particle diameters ranging from 2 to 100 µm.

Example 14

Hot-Melt Extrusion of Amorphous Fine Drug Particles of Carbamazepine

Because the fine drug particles described in Example 13 contain PVP-K30 as a major constituent, which has a glass transition temperature of approximately 150° C., the amorphous microparticle complex will maintain its integrity and thereby its amorphous state if extruded at temperatures of approximately 100° C. or below. The following is an example of a hot-melt extrusion formulation and process by which a homogenous extrudate of individualized and stabilized carbamazepine/PVP-K30 amorphous microparticles can be produced.

Formulation:

| Component | Quantity |
| --- | --- |
| Carbamazepine/PVP-K30 amorphous microparticles (Example 13) | 50% |
| Poloxamer 407 | 35% |
| Sentry Poloyox WSR N80 (PEO) | 15% |

Process:

A Randcastle Microtruder RCP-0750 hot-melt extruder equipped with a 4 mm round die was operated at 20 RPM, 0.1-0.2 Drive Amps at a melt temperature of 60° C. to prepare the composition. All powders were blended in a v-shell blender prior to extrusion. Temperature zones were set as follows: zone 1: 40° C., zone 2: 60° C., zone 3: 60° C., die temperature 60° C. The powder blend was placed in a hopper that is located at the head of a vertical screw such that the material is flood fed by gravity. The residence time of the material in the extruder was approximately two minutes. The extrudate was sheared into approximately one foot sections after exiting the die and placed on aluminum sheets and allowed to cool at ambient conditions. After cooling, the extrudates were milled with a ceramic mortar and pestle and passed through a 250 µm sieve.

Example 15

The following procedure is used for the preparation of HPMC-stabilized amorphous ketoconazole particles using a solvent evaporation technology.

Formulation:

| Component | Quantity |
| --- | --- |
| Ketoconazole (KCZ) | 50% |
| Methocel E5 (HPMC) | 50% |
| Dichloromethane | 2 mL/g solids |

Procedure:

Ketoconazole was dissolved into the organic solvent with the use of an Aquasonic Model 150T ultrasonicator. The ketoconazole solution was then added into a glass mortar which contained the required amount of HPMC. Under a fume hood, the solution was well mixed with the HPMC powder using a glass pestle until a colorless viscous gel was obtained. Most of the solvent was evaporated during this mixing process. The residual solvent was then completely evaporated in a vacuum chamber at temperature of 40° C. and pressure of 500 mTorr to yield a dry solid product. The solid product was subsequently milled in a ceramic media mill containing 20 to 30 ceramic milling balls one centimeter in diameter for approximately one hour at a mill RPM value of 40 to 50. The resulting product was HPMC-stabilized amorphous ketoconazole particles with individual particle diameters ranging from 2 to 50 µm.

Example 16

Hot-Melt Extrusion of Amorphous Fine Drug Particles of Ketoconazole

Because the fine drug particles described in Example 15 contain HPMC as a major constituent, which has a glass transition temperature in the range of 170 to 180° C., the amorphous microparticle complex will maintain its integrity and thereby its amorphous state if extruded at temperatures of approximately 100° C. or below. The following is an example of a hot-melt extrusion formulation and process by which a homogenous extrudate of individualized and stabilized ketoconazole/HPMC amorphous microparticles can be produced.

Formulation:

| Component | Quantity |
| --- | --- |
| Ketoconazole/HPMC E3 amorphous microparticles (Example 15) | 50% |
| Poloxamer 407 | 35% |
| Sentry Poloyox WSR N80 (PEO) | 15% |

Process:

A Randcastle Microtruder RCP-0750 hot-melt extruder equipped with a 4 mm round die was operated at 20 RPM, 0.1-0.2 Drive Amps at a melt temperature of 60° C. to prepare the composition. All powders were blended in a v-shell blender prior to extrusion. Temperature zones were set as follows: zone 1: 40° C., zone 2: 60° C., zone 3: 60° C., die temperature 60° C. The powder blend was placed in a hopper that is located at the head of a vertical screw such that the material is flood fed by gravity. The residence time of the material in the extruder was approximately two minutes. The extrudate was sheared into approximately one foot sections after exiting the die and placed on aluminum sheets and allowed to cool at ambient conditions.

Example 17

The following procedure is used for the preparation of crystalline Danazol nanoparticles by a wet milling technology.

Formulation:

| Component | Quantity |
|---|---|
| Danazol (DNZ) | 75% |
| Polyvinylpyrrolidone (PVP; grade K30) | 25% |
| Deionized water | 10 mL/g solids |

Procedure:

All components listed in the table above were added to a size 000 grinding mill jar (U.S. Stoneware, East Palestine, Ohio) along with 15, 2 cm diameter cylindrical Zirconia grinding media. The grinding jar was capped and allowed to turn on rollers at a rate of 50 RPM for 10 days. The resulting suspension of danazol nanoparticles in water was then rapidly frozen by pouring into liquid nitrogen. The frozen particles were then lyophilized in a VirTis AdVantage benchtop freeze dryer. The resulting product was PVP-stabilized nanocrystals of Danazol with individual particle diameters ranging from 1 μm to 50 nm.

Example 18

Hot-Melt Extrusion of Crystalline Danazol Nanoparticles

Because of the size of and the processing method use to prepare the crystalline danazol nanoparticles, the particles produced are highly aggregated. Therefore, the full benefit of particle size reduction is not achieved by nanocrystal production alone. By melt extruding danazol nanocrystals with a carrier formulation and extrusion parameters that do not solubilize danazol, the stable crystalline form of the drug is not altered and nanoparticle aggregates are broken up and dispersed as individual nanoparticles within the hydrophilic, stabilizing extrudate carrier. The following is an example of a hot-melt extrusion formulation and process by which a homogenous extrudate of individualized and stabilized danazol nanocrystals can be produced.

Formulation:

| Component | Quantity |
|---|---|
| Danazol nanocrystals (Example 17) | 50% |
| Poloxamer 407 | 35% |
| Sentry Poloyox WSR N80 (PEO) | 15% |

Process:

A Randcastle Microtruder RCP-0750 hot-melt extruder equipped with a 4 mm round die was operated at 20 RPM, 0.1-0.2 Drive Amps at a melt temperature of 60° C. to prepare the composition. All powders were blended in a v-shell blender prior to extrusion. Temperature zones were set as follows: zone 1: 40° C., zone 2: 60° C., zone 3: 60° C., die temperature 60° C. The powder blend was placed in a hopper that is located at the head of a vertical screw such that the material is flood fed by gravity. The residence time of the material in the extruder was approximately two minutes. The extrudate was sheared into approximately one foot sections after exiting the die and placed on aluminum sheets and allowed to cool at ambient conditions.

CITATIONS

1. Zhang, F. and J. W. McGinity, *Properties of Sustained-Release Tablets Prepared by Hot-Melt Extrusion.* Pharmaceutical Development and Technology, 1999. 4(2): p. 241-250.
2. Zhang, F. and J. W. McGinity, *Properties of Hot-Melt Extruded Theophylline Tablets Containing Poly(Vinyl Acetate).* Drug Development and Industrial Pharmacy, 2000. 26(9): p. 931-942.
3. Robinson, J. R., J. W. McGinity, and P. Delmas, Effervescent granules and methods for their preparation. June 2000 and November 2003, Ethypharm: U.S. Pat. Nos. 6,071,539 and 6,649,186.
4. Kothrade, S., et al., Method for producing solid dosing forms. 2003: U.S. Pat. No. 6,528,089 WO9927916 DE19753298 EP1035841.
5. Aitken-Nichol, C., F. Zhang, and J. W. McGinity, *Hot Melt Extrusion of Acrylic Films.* Pharmaceutical Research, 1996. 13(5): p. 804-808.
6. Grabowski, S., et al., Solid active extrusion compound preparations containing low-substituted hydroxypropylcellulose. 1999: U.S. Pat. No. 5,939,099 WO9625151 DE19504832 EP0809488.
7. Repka, M. A. and J. W. McGinity, *Hot-melt extruded films for transmucosal & transdermal dung delivery applications.* Drug Delivery Technology, 2004. 4(7): p. 40, 42, 44-47.
8. Repka, M. A., S. L. Repka, and J. W. McGinity, Bioadhesive hot-melt extruded film for topical and mucosal adhesion applications and drug delivery and process for preparation thereof. Apr. 23, 2002: U.S. Pat. No. 6,375, 963.
9. Breitenbach, J. and H. D. Zettler, Method for producing solid sphereical materials containing a biologically active substance. 2000: WO 0024382.
10. de Brabander, C., C. Vervaet, and J. P. Remon, *Development and evaluation of sustained release mini-matrices prepared via hot melt extrusion.* Journal of Controlled Release, 2003. 89(2): p. 235-247.
11. de Brabander, C., et al., *Bioavailability of ibuprofen from hot-melt extruded mini-matrices.* International Journal of Pharmaceutics, 2004. 271(1-2): p. 77-84.
12. Rosenberg, J. and J. Breitenbach, The production of active substance compositions in the form of a solid solution of the active substance in a polymer matrix, and active substance compositions produced by this process. 1998: U.S. Pat. No. 5,741,519 WO 9629061 EP 0760654 DE 19509807.
13. Six, K., et al., *Characterization of Solid Dispersions of Itraconazole and Hydroxypropylmethylcellulose Prepared by Melt Extrusion, Part II.* Pharmaceutical Research, 2003. 20(7): p. 1047-1054.
14. Six, K., et al., *Thermal Properties of Hot-Stage Extrudates of Itraconazole and Eudragit E100Phase Separation and Polymorphism.* Journal of Thermal Analysis and calorimetry, 2002. 68: p. 591-601.
15. Six, K., et al., *Identification of Phase Separation in Solid Dispersions of Itraconazole and Eudragit E100 Using Microthermal Analysis.* Pharmaceutical Research, 2003. 20(1): p. 135-138.
16. Six, K., et al., *Increased Physical Stability and Improved Dissolution Properties of Itraconazole, a Class II Drug, by Solid Dispersions that Combine Fast-and Slow-Dissolving Polymers.* Journal of Pharmaceutical Sciences, 2004. 93(1): p. 124-131.
17. Verreck, G., et al., *Characterization of solid dispersions of itraconazole and hydroxypropylmethylcellulose prepared by melt extrusion—part I.* International Journal of Pharmaceutics, 2003. 251(1-2): p. 165-174.
18. Brewster, M., et al., Solid dispersion comprising two different polymer matrixes. 2004: WO2004004683.

19. Baert, L. E. C., G. Verreck, and D. Thone, *Antifungal compositions with improved bioavailability*. 2003: U.S. Pat. No. 6,509,038, WO9744014, U.S. Pat. No. 6,509,038 (B2), US2001007678 (A1), EE9800304 (A), TR9801225T (T2), EE3902 (B1).
20. Rambali, B., et al., *Itraconazole Formulation Studies of the Melt-Extrusion Process with Mixture Design*. Drug Development and Industrial Pharmacy, 2003. 29(6): p. 641-652.
21. Verreck, G., et al., *The Use of Three Different Solid Dispersion Formulations Melt Extrusion, Film-Coated Beads, and a Glass Thermoplastic System—To Improve the Bioavailability of a Novel Microsomal Triglyceride Transfer Protein Inhibitor*. Journal of Pharmaceutical Sciences, 2004. 93(5): p. 1217-1228.
22. Hulsmann, S., et al., *Melt extrusion—an alternative method for enhancing the dissolution rate of 17(beta)-estradiol hemihydrate*. European Journal of Pharmaceutics and Biopharmaceutics, 2000. 49(3): p. 237-242.
23. Forster, A., J. Hempenstall, and T. Rades, *Characterization of glass solutions of poorly water soluble drugs produced by melt extrusion with hydrophilic amorphous polymers*. Journal of Pharmacy and Pharmacology, 2001. 53: p. 303-315.
24. Kearney, A. S., et al., *Effect of polyvinylpyrrolidone on the crystallinity and dissolution rate of solid dispersions of the antiinflammatory CI-987*. International Journal of Pharmaceutics, 1994. 104(2): p. 169-174.
25. Nykamp, G., U. Carstensen, and B. W. Muller, *Jet milling—a new technique for microparticle preparation*. International Journal of Pharmaceutics, 2002. 242(1-2): p. 79-86.
26. Carstensen, U. and B. W. Mueller, New process for the preparation of microparticles, useful e.g. for controlled drug release, comprises encapsulating active agent in biodegradable polymer under heating, cooling and milling in two stages to a fine powder. 2002: DE10061932.
27. Reverchon, E., *Supercritical antisolvent precipitation of micro-and nano-particles*. Journal of Supercritical Fluids, The, 1999. 15(1): p. 1-21.
28. Palakodaty, S. and P. York, *Phase Behavioral Effects on Particle Formation Processes Using Supercritical Fluids*. Pharmaceutical Research, 1999. 16(7): p. 976-985.
29. Bleich, J. and B. W. Mueller, *Production of drug loaded microparticles by the use of supercritical gases with the Aerosol Solvent Extraction System (ASES) process*. Journal of Microencapsulation, 1996. 13(2): p. 131-139.
30. Chen, X., et al., *Preparation of cyclosporine A nanoparticles by evaporative precipitation into aqueous solution*. International Journal of Pharmaceutics, 2002. 242 (1-2): p. 3-14.
31. Chattopadhyay, P. and R. B. Gupta, *Production of griseofulvin nanoparticles using supercritical CO2 antisolvent with enhanced mass transfer*. International Journal of Pharmaceutics, 2001. 228(1-2): p. 19-31.
32. Ghaderi, R., P. Artursson, and J. Carlfors, *Preparation of biodegradable microparticles using solution-enhanced dispersion by supercritical fluids (SEDS)*. Pharmaceutical research, 1999. 16(6): p. 676-681.
33. Phillips, E. M. and V. J. Stella, *Rapid expansion from supercritical solutions: application to pharmaceutical processes*. International Journal of Pharmaceutics, 1993. 94(1-3): p. 1-10.
34. Hu, J., et al., *Improvement of Dissolution Rates of Poorly Water Soluble APIs Using Novel Spray Freezing into Liquid Technology*. Pharmaceutical Research, 2002. 19(9): p. 1278-1284.
35. Evans, J. C., et al., *Preparation of nanostructured particles of poorly water soluble drugs via a novel ultra-rapid freezing technology*. Polymeric Materials Science and Engineering (2003), 2003. 89: p. 742.
36. Zimon, A. D., *Adhesion of Dust and Powder*. 1982, New York: Consultants Bureau (Plenum). pp 93-144.
37. French, D. L., D. A. Edwards, and R. W. Niven, *The influence of formulation of emission, deaggregation and deposition of dry powders for inhalation*. Journal of Aerosol Science, 1996. 27: p. 769-783.
38. Liu, J. and P. J. Stewart, *Deaggregation during the Dissolution of Benzodiazepines in Interactive Mixtures*. Journal of Pharmaceutical Science, 1998. 87(12): p. 1632-1638.
39. Ticehurst, M. D., et al., *Characterisation of the influence of micronisation on the crystallinity and physical stability of revatropate hydrobromide*. International Journal of Pharmaceutics, 2000. 193: p. 247-259.
40. Hu, J., K. P. Johnston, and I. Williams, Robert O., *Rapid release tablet formulation of micronized danazol powder produced by spray-freezing into liquid (SFL)*. Journal of Drug Delivery Science and Technology, 2004. 14(4): p. 305-311.
41. Liversidge, G. G. and P. Conzentino, *Drug particle size reduction for decreasing gastric irritancy and enhancing absorption of naproxen in rats*. International Journal of Pharmaceutics, 1995. 125(2): p. 309-313.
42. Liversidge, G. G. and K. C. Cundy, *Particle size reduction for improvement of oral bioavailability of hydrophobic drugs. Part 1: Absolute oral bioavailability of nanocrystalline danazol in beagle dogs*. International Journal of Pharmaceutics, 1995. 125: p. 91-97.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. A process for preparing a hot-melt extruded pharmaceutical composition comprising drug-containing particles dispersed in a stabilizing and non-solubilizing carrier, the process comprising:
    providing drug-containing particles of a therapeutic compound, wherein said particles have a mean particle diameter of 100 microns or less and comprise one or more amorphous or crystalline therapeutic compounds dispersed in one or more adjunct stabilizers;
    admixing said drug-containing particles with a stabilizing and non-solubilizing hot-melt extrudable carrier that does not solubilize, or solubilizes 10% drug weight or less of, the drug containing particles to form a particle-carrier admixture; and
    mixing and hot-melting extruding the charges particle-carrier admixture to form the hot-melt extruded pharmaceutical composition; wherein a substantial majority of the fine drug particles are not agglomerated or aggregated as a result of the step of hot-melt extruding.

2. The process of claim 1 further comprising: preparing the fine drug-containing particles by mechanical milling; solution based phase separation technique; freezing technique or a combination thereof.

3. The process of claim 2 further comprising: preparing the fine drug-containing particles by ball mill, jet mill, grinding, mortar and pestle grinding, spray drying, combined emulsification and evaporation, combined emulsification and solvent extraction, complex coacervation, gas anti-solvent precipitation, precipitation with a compressed antisolvent, aerosol solvent extraction system, evaporative precipitation into aqueous solution, supercritical antisolvent, solution-enhanced dispersion by supercritical fluids, rapid expansion from supercritical to aqueous solutions, pressure induced phase separation, spray freezing into liquid, ultra rapid freezing, anti-solvent precipitation or a combination thereof.

4. The process of claim 1, the process further comprising: determining the temperature at which the therapeutic compound dissolves into the stabilizing and non-solubilizing hot-melt extrudable carrier; and/or determining the temperature at which amorphous drug in the fine drug-containing particles begins to recrystallize.

5. The process of claim 4, wherein the therapeutic compound is amorphous, and the step of hot-melt extruding is conducted at a temperature that is at least 10° C. below the temperature at which the therapeutic compound in the fine drug-containing particles begins to recrystallize.

6. The process of claim 5, wherein the step of hot-melt extruding is conducted at a temperature wherein the stabilizing and non-solubilizing hot-melt extrudable carrier melts.

7. The process of claim 4, wherein the therapeutic compound is crystalline, and the step of hot-melt extruding is conducted at a temperature that is at least 10° C. below the temperature at which the therapeutic compound dissolves into the stabilizing and non-solubilizing hot-melt extrudable carrier.

8. The process of claim 7, wherein the step of hot-melt extruding is conducted at a temperature wherein the stabilizing and non-solubilizing hot-melt extrudable carrier melts.

9. The process of claim 1, wherein the drug-containing particles comprise a therapeutic compound and one or more adjunct stabilizers.

10. The process of claim 9, wherein the adjunct stabilizer is selected from the group consisting of sorbitan esters, polyoxyethylene sorbitan fatty acid esters, polyoxyethylene alkyl ethers, poloxamers (polyethylene-polypropylene glycol block copolymers), sucrose esters, sodium lauryl sulfate, oleic acid, lauric acid, vitamin E TPGS, polyoxyethylated glycolysed glycerides, dipalmitoyl phosphadityl choline, glycolic acid and salts, deoxycholic acid and salts, sodium fusidate, cyclodextrins, polyethylene glycols, polyglycolyzed glycerides, polyvinyl alcohols, polyacrylates, polymethacrylates, polyvinylpyrrolidones, phosphatidyl choline and derivatives, and cellulose derivatives and a combination thereof.

11. The process of claim 10, wherein the adjunct stabilizer is comprised of a polyvinylpyrrolidone.

12. The process of claim 1, wherein the stabilizing and non-solubilizing carrier is selected from the group consisting of a poloxamer, polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcellulose; hydroxyalkylcellulose; hydroxyalkyl alkylcellulose; starch; pectin; polysaccharide; lipid; wax; mono, di, and tri glycerides; cetyl alcohol; steryl alcohol; parafilm wax; hydrogenated vegetable and castor oil; glycerol monostearte; polyolefin; xylitol; mannitol; sorbitol; alpha-hydroxyl acid; enteric polymer; and a combination thereof.

13. The process of claim 12, wherein the stabilizing and non-solubilizing carrier is comprised of polyethylene oxide.

14. The process of claim 1, wherein the particles have a mean particle diameter of 50 microns or less.

15. The process of claim 14, wherein the particles have a mean particle diameter of 10 microns or less.

16. The process of claim 1, wherein the particles have a mean particle diameter of 1 micron or less.

17. The process of claim 1, wherein greater than 75% of the particles have an average diameter of less than about 20 microns.

18. The process of claim 17, wherein greater than 75% of the particles have an average diameter of less than about 5 microns.

19. The process of claim 18, wherein greater than 75% of the particles have an average diameter of less than about 1 micron.

20. The process of claim 1, wherein 5% by number or less of the particles are present in the composition in agglomerated form.

21. The process of claim 1, wherein the fine particles have been prepared by spray drying, mechanical milling, solution based phase separation technique, freezing technique, anti-solvent precipitation, or a combination thereof.

22. The process of claim 21, wherein the fine particles have been prepared by spray drying.

23. The process of claim 1, wherein the therapeutic compound is amorphous.

24. The process of claim 23, which has been hot-melt extruded at a temperature that is at least 10° C. below the temperature at which the therapeutic compound in the fine particles begins to recrystallize.

25. The process of claim 1, wherein the therapeutic compound is crystalline.

26. The process of claim 25, which has been hot-melt extruded at a temperature that is at least 10° C. below the temperature at which the therapeutic compound dissolves into the stabilizing and non-solubilizing hot-melt extrudable carrier.

27. The process of claim 1, wherein the composition has been hot-melt extruded at a temperature that is 100° C. or less.

28. The process of claim 1, wherein the therapeutic compound is itraconazole.

* * * * *